US008220260B2

(12) United States Patent
Harris

(10) Patent No.: US 8,220,260 B2
(45) Date of Patent: Jul. 17, 2012

(54) FLUID TRANSMISSION

(76) Inventor: Martin Russell Harris, Windsor (AU)

( * ) Notice: Subject to any disclaimer, the term of this patent is extended or adjusted under 35 U.S.C. 154(b) by 907 days.

(21) Appl. No.: 12/065,203

(22) PCT Filed: Sep. 4, 2006

(86) PCT No.: PCT/AU2006/001294

§ 371 (c)(1), (2), (4) Date: Aug. 26, 2008

(87) PCT Pub. No.: WO2007/025353

PCT Pub. Date: Mar. 8, 2007

(65) Prior Publication Data

US 2009/0071137 A1 Mar. 19, 2009

(30) Foreign Application Priority Data

Sep. 2, 2005 (AU) ................................ 2005904837
Sep. 4, 2006 (WO) ................ PCT/AU2006/001294

(51) Int. Cl.
*A63H 3/00* (2006.01)
*A61F 2/46* (2006.01)

(52) U.S. Cl. ........................................................ 60/533

(58) Field of Classification Search ..................... 60/533
See application file for complete search history.

(56) References Cited

U.S. PATENT DOCUMENTS

| | | | | | |
|---|---|---|---|---|---|
| 4,057,928 | A | * | 11/1977 | Terzian | 446/198 |
| 4,372,297 | A | | 2/1983 | Perlin | |
| 4,685,447 | A | | 8/1987 | Iversen et al. | |
| 5,176,683 | A | | 1/1993 | Kimsey et al. | |
| 5,807,358 | A | * | 9/1998 | Herweck et al. | 604/320 |
| 5,861,870 | A | | 1/1999 | Anderson | |
| 2005/0072763 | A1 | | 4/2005 | Delgado | |

FOREIGN PATENT DOCUMENTS

| | | |
|---|---|---|
| EP | 1 586 778 | 10/2005 |
| GB | 2 093 760 | 9/1982 |
| GB | 2 236 686 | 4/1991 |
| GB | 2 335 467 | 9/1999 |
| JP | 2003-211539 | 7/2003 |
| WO | WO 92/18070 | 10/1992 |

OTHER PUBLICATIONS

Supplementary European Search Report for Application No. EP 06 77 4923 dated Nov. 5, 2008.
International Search Report for International Application No. PCT/AU2006/001294 mailed Nov. 22, 2006.

* cited by examiner

*Primary Examiner* — Thomas E Lazo
(74) *Attorney, Agent, or Firm* — Pearl Cohen Zedek Latzer, LLP

(57) ABSTRACT

A fluid transmission that employs a fluid to transmit a force, comprising a conduit for the fluid made from heat shrink polymer tubing, wherein at least a portion of the heat shrink polymer tubing is shrunken, whereby the force can be transmitted by the fluid from a first or proximal end of the conduit to a second or distal end of the conduit. Also, an actuator and methods for manufacturing the transmission and actuator.

11 Claims, 21 Drawing Sheets

FLUID TRANSMISSION

CROSS-REFERENCE TO RELATED APPLICATIONS

This application is a National Phase Application of PCT International Application No. PCT/AU2006/001294, entitled "A FLUID TRANSMISSION", International Filing Date Sep. 4, 2006, published on Mar. 8, 2007 as International Publication No. WO 2007/7025353, which in turn claims priority from Australian Patent Application No. 2005904837, filed Sep. 2, 2005, both of which are incorporated herein by reference in their entirety.

FIELD OF THE INVENTION

The present invention relates to a fluid transmission for the transmission of force, of particular use in hydraulic or pneumatic actuators.

FIELD OF THE INVENTION

Transmission of an actuating force by the movement of fluid through pipes is employed where smooth and linear motion is required. The most common method uses a cylinder enclosing a piston at the driven end, and a fluid pump (which may also comprise a piston and cylinder) at the driver end.

Pneumatic systems use an actuating fluid in the form of a gas such as air, so leakage of the actuating fluid is a lesser problem than where hydraulic oils are employed. However, hydraulic systems (where the actuating fluid is in the form of a liquid such as water or oil) can produce greater force and, as liquids are effectively incompressible, greater precision and linearity of motion.

Both pneumatic and hydraulic systems have well defined areas of application. Their most common embodiments require precision cylinder bores and pistons. They also rely on the maintenance of fluid seals, typically in the form of which are generally elastomer "o"-rings. Systems that do not require a sliding seal exist (e.g. the pneumatic bellows systems of a pianola) but are not in widespread use.

Electromagnetic linear drives that employ linear motors or leadscrews and piezoelectric linear actuators (e.g. Burleigh inchworm drives) are widely used but are complex. Pressure operated linear actuator systems are generally less expensive.

Hydraulic (or pneumatic) drivers and actuators can also be made from impermeable flexible bags or sacks connected by flexible pipes. The bags or sacks can be made from elastomeric polymers or from inelastic but flexible material; the latter can be made from a more general class of material than the former. In both cases, the expansion of the bag under pneumatic or hydraulic action can be used to exert a force where desired.

Such systems can be versatile and potentially of low cost. They are not widely used, however, possibly because they are not easily made. In particular, the fabrication of small examples can be difficult and ensuring that the seals do not leak can be time consuming.

Another feature of certain fluid actuating systems is the manner in which the conveniently obtainable output power/force scales as the size is reduced. For example, the maximum force able to be exerted by an electromagnet is proportional to the volume of the magnetic material of which it is composed (which scales as the cube of its linear dimensions.) Hence, reducing the size of a electromagnetic solenoid or electric (magnetic) motor by a factor of 10 reduces force or power output by a factor of 1000. This inverse cube power law also applies to piezo and many other motors. Currently, the smallest readily available electromagnetic motor is 1.8 mm in diameter and 44 mm long, but costs around AU$1,000 with the required gearbox to produce reasonable torque/force.

In the case of electrostatic motors, the force available to drive the motor is proportional to the square of the linear dimensions, that is, the area of the two attracting plates in an electrostatic motor. Reduction in size of such systems to a tenth reduces the force or power to 1/100, a factor of 10 better than an electromagnetic motor. For this reason electrostatic actuating is almost universally employed in nanomotors. These nanomotors are generally in the form of vibrating resonant "comb drives" formed by photolithography and deep etching from silicon wafers. The silicon torsion bridge suspension is strong and highly elastic, so quite high amplitude vibration can be achieved. However, the amplitudes of the vibrations are ultimately limited by the torque produced by the electrostatic forces—which is small—and are only maximized if the waveform of the drive voltage is applied at the resonant frequency.

SUMMARY OF THE INVENTION

According to a first broad aspect of the invention, the present invention provides a fluid transmission that employs a fluid to transmit a force, comprising a conduit for the fluid made from heat shrink polymer tubing, wherein at least a portion of the heat shrink polymer tubing is shrunken, whereby the force can be transmitted by the fluid from a first or proximal end of the conduit to a second or distal end of the conduit.

The conduit may additionally include (at the proximal and/or distal end) one or more portions of unshrunk or semishrunk heat shrink polymer tubing, either integral with the shrunken portion or comprising separate portions of heat shrink polymer tubing.

In particular, the transmission may include a driver section formed from unshrunk or semishrunk heat shrink polymer tubing and located at the proximal end. The transmission may include one or more driven section formed from unshrunk or semishrunk heat shrink polymer tubing and located at the distal end.

Thus, driver section is analogous with a master cylinder in a hydraulic system, and the driven section is analogous with a slave cylinder in a hydraulic system. The flow of the fluid (whether hydraulic or pneumatic) between the driver section and the driven section may be modified by other components located between the driver section and the driven section of the transmission or located elsewhere in the transmission. Such components may be internal to the heat shrink polymer tubing (and acting within shrunken or semishrunken sections of tubing), or external to the heat shrink polymer tubing (and acting on unshrunk, semishrunken or shrunken sections of tubing).

As with electrostatic motors, the force transmitted by the transmission is proportional to the square of the linear dimensions, that is, the area of the driven section's opposing walls that are pushed apart by the pressurised fluid. Hence, reduction of the size of the transmission by a factor of 10 reduces the force or power by a factor of 100.

In one embodiment, the transmission includes a spring mechanically coupled to either a driver section or a driven section of the transmission so as to react against expansion of the driver or driven section.

The heatshrink process may be carried out, in order to shrink or partially shrink the heat shrink polymer tubing, by means of a hot air gun or other source of hot gas (including by placing the polymer tubing in an oven). It may also be carried out by radiant heat or by contact with a hot object.

The thermal gradients employed for the heatshrink process may be arranged so that the deformation of the polymer tubing leaves it in a shape adapted for the intended application. For example a portion of polymer tubing that it is desired remain unshrunk may be protected from the hot air used for shrinking. This can be done, for example, by locating that portion in a slot or other constraining cavity (and performed either cold or after prior heating of that section of polymer tubing), or holding the desired portion between the jaws of a pair of pliers or the like. The shrunken tube when in its hot pliable state may also be formed into a desired shape in a jig or loom to facilitate subsequent assembly processes.

In one embodiment, the conduit is a first conduit and the fluid transmission includes one or more additional like conduits.

According to another broad aspect, the present invention provides a method of manufacturing a fluid transmission, comprising: forming a conduit for the fluid from heat shrink polymer tubing; and heat shrinking at least a portion of the heat shrink polymer tubing; whereby a force can be transmitted by the fluid from a first or proximal end of the conduit to a second or distal end of the conduit.

In one embodiment, the method includes forming at least one integral driver section comprising unshrunken or semishrunken heat shrink polymer tubing. In some embodiments, the method includes forming at least one integral driven section comprising unshrunken or semishrunken heat shrink polymer tubing.

The invention also provides various devices for achieving certain desired mechanical effects and employing a fluid transmission as described above, as will be apparent from the description of various embodiments.

According to a further aspect of the invention there is provided an actuator, comprising:

- a plurality of pivotably connected members;
- at least one expandable bag located between a pair of said members; and
- a fluid conduit in fluid communication with said expandable bag for expanding said bag by transmitting a fluid to said bag, said fluid conduit comprising heat shrink polymer tubing at least a portion of which is shrunken;
- wherein expansion of said bag urges said pair of members apart.

In one particular embodiment, the actuator includes four members connected as a quadrilateral. The quadrilateral may be, for example, a parallelogram or a trapezium.

A plurality of such actuators can be coupled according to the present invention to form a complex or compound actuator.

According to a further aspect of the invention there is provided a device comprising an actuator as described above. The device may be, for example, a toy in which the actuator is used to actuate movement of a portion of the toy (such as a limb). In other examples, the device is a camera, a robot, a microscope or a mobile telephone.

According to a further aspect of the invention there is provided a method for manufacturing a fluid transmission, comprising:

- selectively masking a length of heat shrink polymer tubing; and
- heating said heat shrink polymer tubing to shrink a portion or portions of said heat shrink polymer tubing that is not masked;
- whereby at least two unshrunken sections and at least one shrunken section are formed, to provide a driver bag and a driven bag with a fluid conduit therebetween.

BRIEF DESCRIPTION OF THE DRAWING

In order that the invention may be more clearly ascertained, embodiments will now be described, by way of example, with reference to the accompanying drawing, in which.

DETAILED DESCRIPTION

Figure 1:
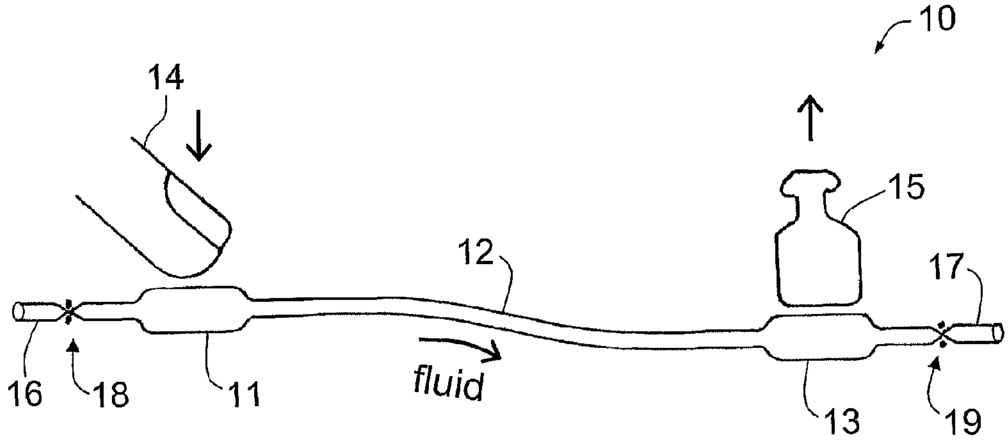
FIG. 1 is a view of a fluid transmission according to an embodiment of the present invention.

FIG. 1 is a view of a simple fluid transmission 10 according to an embodiment of the present invention. The transmission includes an unshrunk driver section 11 of heat shrink polymer tubing connected by a shrunk section 12 to another unshrunk driven section 13; these three sections are integral with one another. The transmission 10 is filled with a suitable fluid, which might in many applications be water, air or oil. However, the fluid can be selected according to intended use, compatibility with the material of the polymer tubing and likely environmental conditions in which it will be used.

Pressure applied to driver section 10 by finger 14 forces fluid along shrunk section 12 and expands driven section 13, thereby raising weight 15.

The transmission 10 includes shrunken sections 16 and 17 that form seals (to prevent the escape of the hydraulic or pneumatic fluid) by means of plugs or crimps 18 and 19. These ends may be sealed by various means, including shrinking the end down onto a short section of rod, heat sealing or melting the end, and—as illustrated in FIG. 1—providing an external crimping device. This last option was found to be the best. A U-shaped or e-shaped piece of metal strip was used. Shrinking onto the tubing was found to be useful to change between tubing sizes and to allow the incorporation of other fluid devices.

Figure 2:
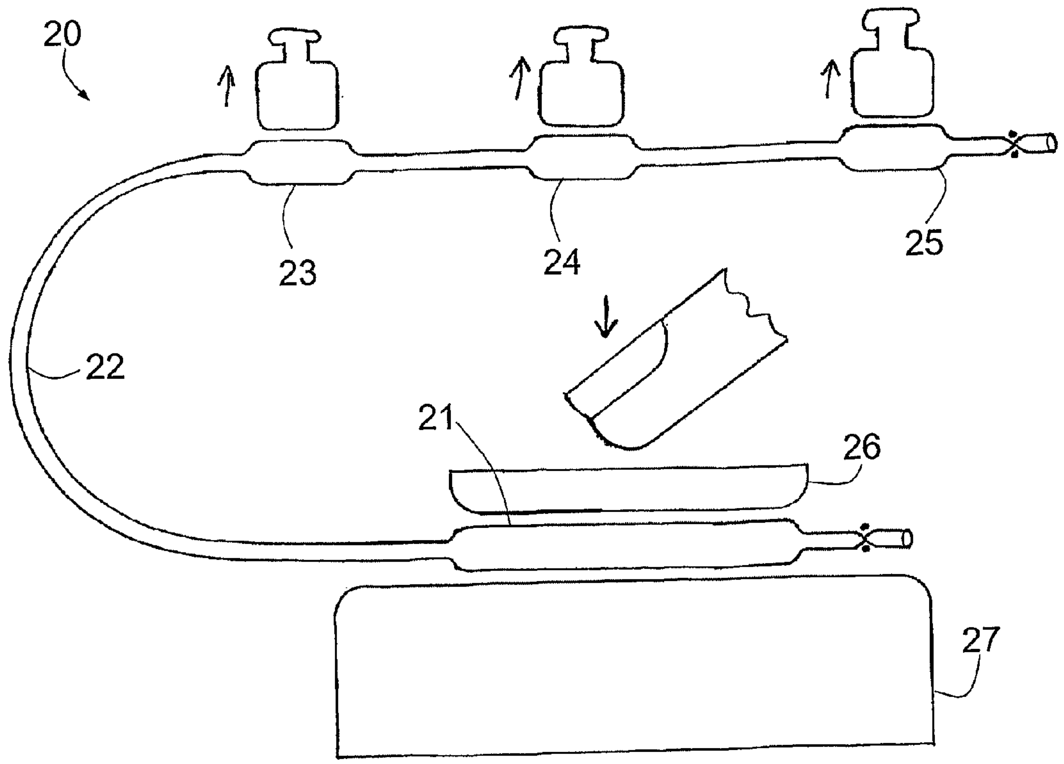
FIG. 2 is a view of a fluid transmission according to another embodiment of the present invention.

FIG. 2 is a view of a fluid transmission 20 according to another embodiment of the invention, in which a force applied at unshrunken driver bag 21 can move the fluid along integral shrunken pipe 22 and to produce motion of a plurality of integral unshrunken bag sections 23, 24, 25. (Plates 26 and 27 are provided above and below driver bag 21, respectively, to distribute the force applied to the driver bag 21.)

Clearly the actuated (i.e. driven) sections 23, 24 and 25 can be widely separated from one another. The volume of fluid that can be provided by the compression of driver bag 21 is at least as great as the volume required to actuate sections 23, 24 and 25.

Figure 3A:
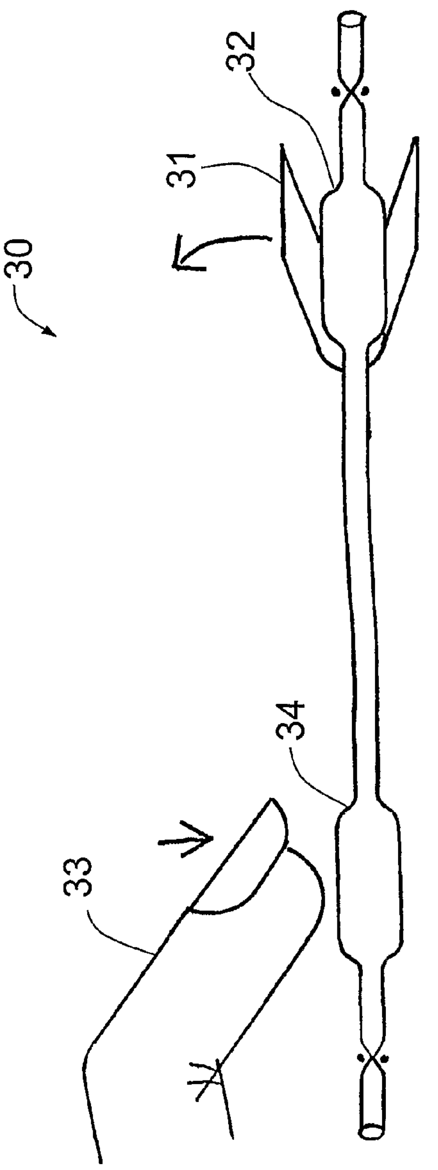
FIGS. 3*a*, 3*b*, 3*c* and 3*d* are views of a fluid transmission according to another embodiment of the present invention.

FIG. 3*a* is a view of a fluid transmission 30 according to another embodiment of the present invention. The fluid transmission 30 includes a spring 31 in the form of a folded metal sheet that partially encloses a driven hydraulic bag 32. When pressure is released from the driver bag 34 (such as by the lifting of the pressure of finger 33) the spring 31 forces fluid in the transmission 30 back to the driver bag 34, connected integrally to the driver bag 34, and is thereby inflated.

Figure 3B:
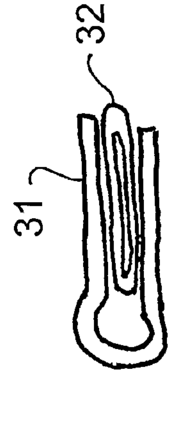
Figure 3C:
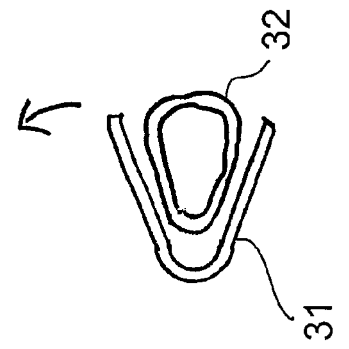
Figure 3D:
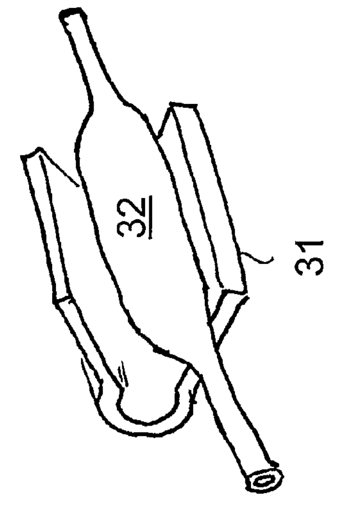

FIGS. 3*b* and 3*c* are cross-sectional views of spring 31 and driven bag 32. In these views, the spring 31 and driven bag 32 are shown, respectively, compressed and expanded (or relaxed). FIG. 3*d* is an isometric view of spring 31 and driven bag 32, shown expanded.

Figure 4:
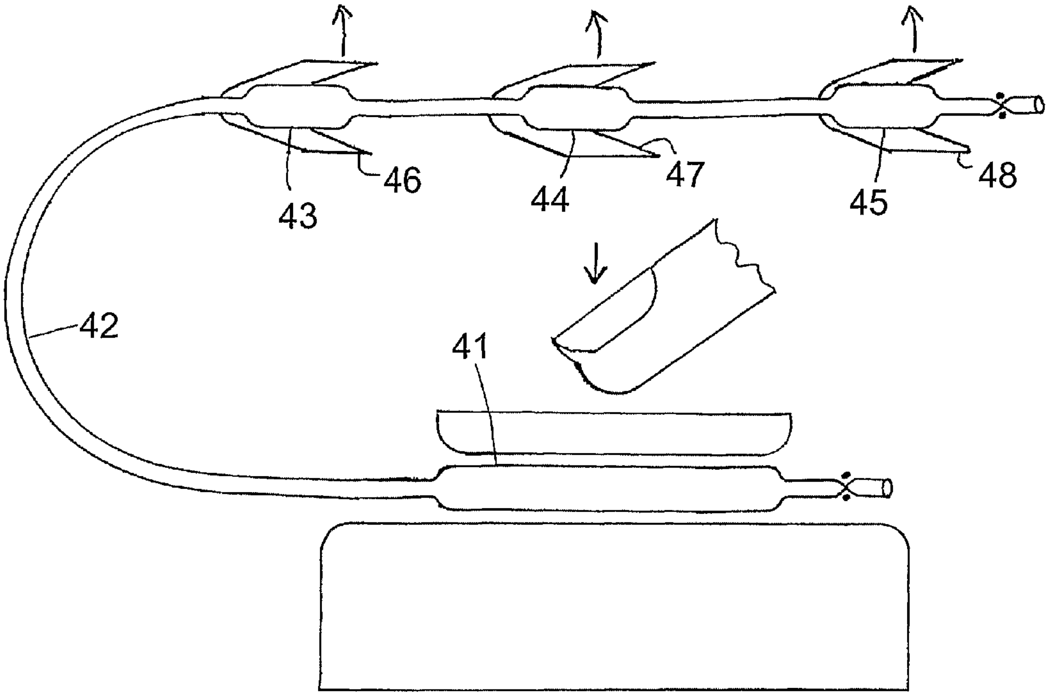
FIG. 4 is a view of a fluid transmission according to another embodiment of the present invention.

FIG. 4 is a view of a fluid transmission 40 according to another embodiment of the invention. Fluid transmission 40 includes a driver bag 41 connected by integral shrunken polymer tubing 42 to three remote driven bags 43, 44 and 45; the driven bags are located in respective spring clips 46, 47 and 48. Driver bag 41 is arranged for actuating driven bags 43, 44 and 45 and hence clips 46, 47 and 48. As will be appreciated, if the spring constants of the clips 46, 47 and 48 differ, or if the lengths of the driven bags differ, it is possible to produce a sequence of operation of movements of the three driven bags. For example, if the driven bags have identical lengths, but the clips increase in stiffness in the order 46, 47, 48, the driven bags will be actuated in the sequence 45, 44, 43. Deflation of these driven bags—once the force is released from driver bag 41—will reversed and hence 43, 44, 45 (an effect that may be referred to as FILO: first in, first out).

In the various embodiments described herein, fluid flow within the conduit of the fluid transmission can be modified or controlled by locating constriction elements or valves in the conduit. During manufacture, shrinkage of the heat shrink polymer tubing can be employed to form or to enclose such devices. These devices may be used to produce a variant of effects.

Figure 5:
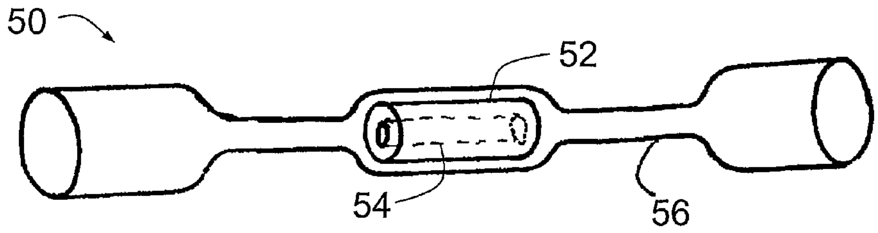
FIG. 5 is a view of a flow restriction device within a length of conduit according to another embodiment of the present invention.

For example, FIG. 5 is a view of a flow restriction device according to an embodiment of the invention in situ within a length of conduit, generally at 50. The restriction device 52 comprises a short rod with a small bore 54 passing axially along the length of the rod, and can be heat sealed in position inside the length of conduit 56. This flow restriction device is considerably more convenient and reproducible than an externally located flow restriction device.

Figure 6:
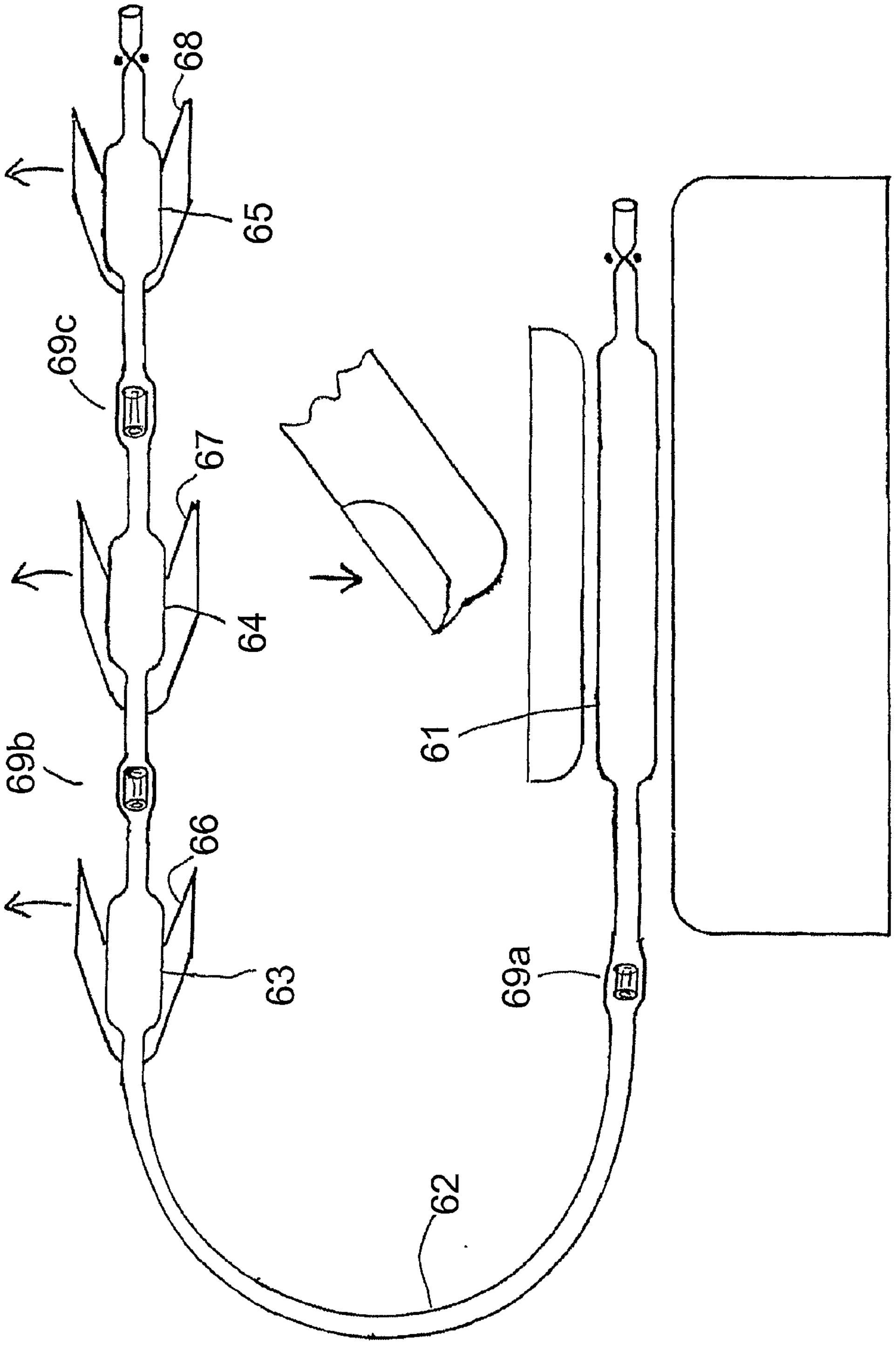
FIG. 6 is a view of a fluid transmission according to another embodiment of the present invention.

Thus, FIG. 6 is a view of a fluid transmission 60 according to another embodiment of the invention that includes a flow restriction device. The transmission 60 includes a driver bag 61 integrally connected to three driven bags 63, 64 and 65 by means of integral shrunken polymer tubing 62. The driven bags 63, 64 and 65 are located in respective spring clips 66, 67 and 68 (of identical spring constant). In the shrunken polymer tubing 62 are located three flow restriction device: a first flow restriction device 69*a* between driver bag 61 and driven bag 63, a second flow restriction device 69*b* between driven bag 63 and driven bag 64, and a third flow restriction device 69*c* between driven bag 64 and driven bag 65.

Compression of bag 61 pumps fluid into the driven bags 63, 64, 65 but the sequence of operation is 63, 64, 65 owing to the restriction of flow. The deflation sequence is also 63, 64, 65.

Figure 7:
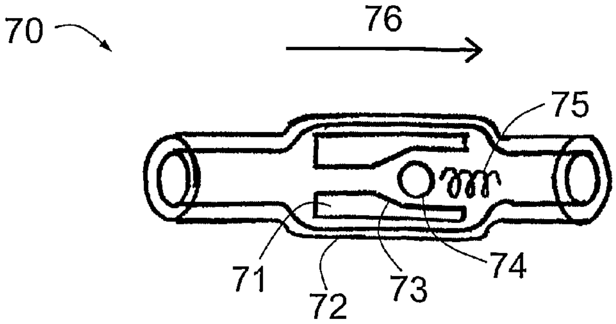
FIG. 7 is a cross-sectional view of a one-way valve encased in a shrunken section of heat shrink polymer tubing according to an embodiment of the invention.

FIG. 7 is a cross-sectional view 70 of a one-way valve encased in a shrunken section of heat shrink polymer tubing according to an embodiment of the invention, which may be regarded as a hydraulic analogue of a diode. A short, rigid tube 71 (constituting the valve body) is encased in heatshrink 72. One end of the interior of this tube is enlarged to form a valve seat 73. A ball 74 is positioned in this expanded section. A spring 75 may be held in a position to press the ball back into the valve seat.

Fluid can flow with minimal resistance in the direction shown by arrow 76. Fluid flow in the opposite direction encounters considerable resistance, but it may be desirable not to block it completely.

It may also be desirable to produce one way valves in which a part of the valve permits a pre-determined back flow rate. This could be effected, for example, by providing the tube 71 with an axial bore for allowing back flow, in which the diameter of the bore is selected to set the back flow rate. It will also be appreciated that mushroom valves, poppet valves, flap valves could be employed.

Figure 8:
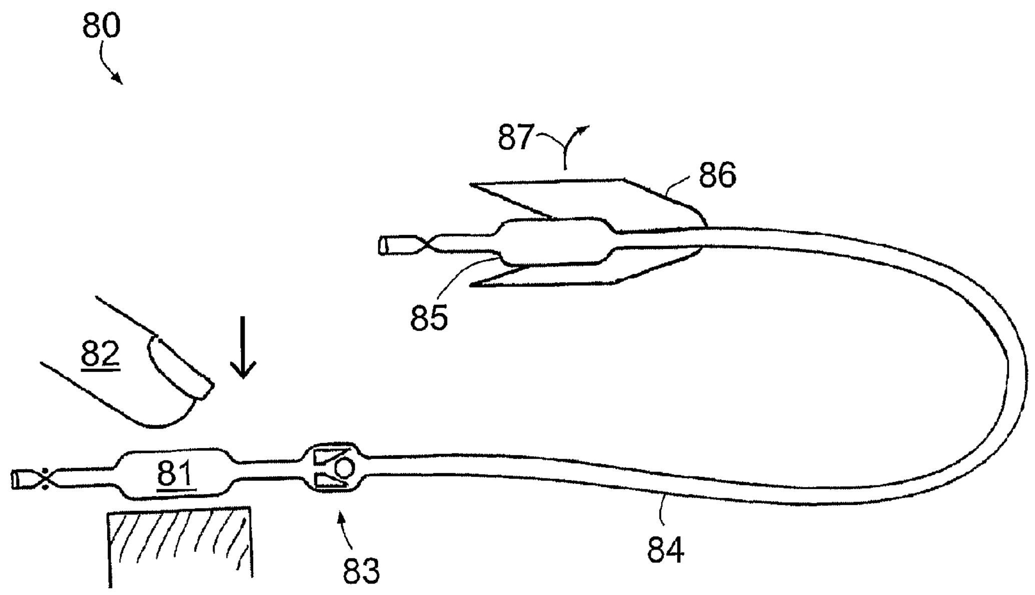
FIG. 8 is a view of a fluid transmission according to another embodiment of the present invention.

FIG. 8 is a view of a fluid transmission 80 according to an embodiment of the invention that includes a one-way valve. Transmission 80 could be used to lift a lid quickly but then lower it slowly. When the driver bag 81 is compressed (such as by a finger 82), the fluid in the transmission—which may be water—passes with minimal resistance in the forward direction through the one-way valve 83 and along tube 84.

The fluid then passes into the driven bag 85 which expands against the spring 86, thereby raising, for example, a lid (not shown) in direction 87.

When the force is removed from driver bag 81, the fluid is able to flow back through the higher reverse resistance of valve 83 and into the driver bag 81, slowly lowering (for example) the lid.

Figure 9:
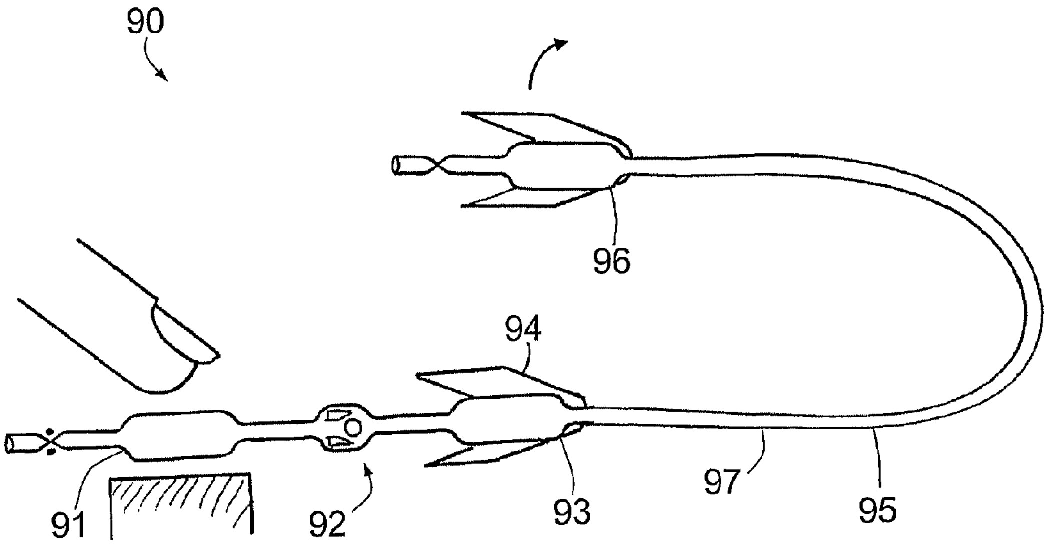
FIG. 9 is a view of a fluid transmission according to another embodiment of the present invention.

FIG. 9 is a view of a fluid transmission 90 according to another embodiment of the invention, which is similar to that of FIG. 8 but with extra components to provide a still more controlled and uniform raising of the lid.

These components also act to protect the transmission from accidental excess digital force overload.

The transmission 90 is essentially identical in its components and operation with that shown in FIG. 8 with the addition of a further driven bag (the hydraulic analogue of a capacitor) between the one-way valve 92 (cf. one-way valve 82 in FIG. 8) and driven bag 96 (cf. driven bag 86 in FIG. 8). Fluid from driver bag 91 flows through one-way valve 92 under finger pressure and expands further driven bag 93 against the pressure of further spring 94. The fluid from the further driven bag 93 moves along heat shrink conduit portion 95 to actuate the required motion by expanding driven bag 96. Optionally, a flow restrictor may be located—if desired—in the conduit 95 at 97 to control the activation rate.

Figure 10:
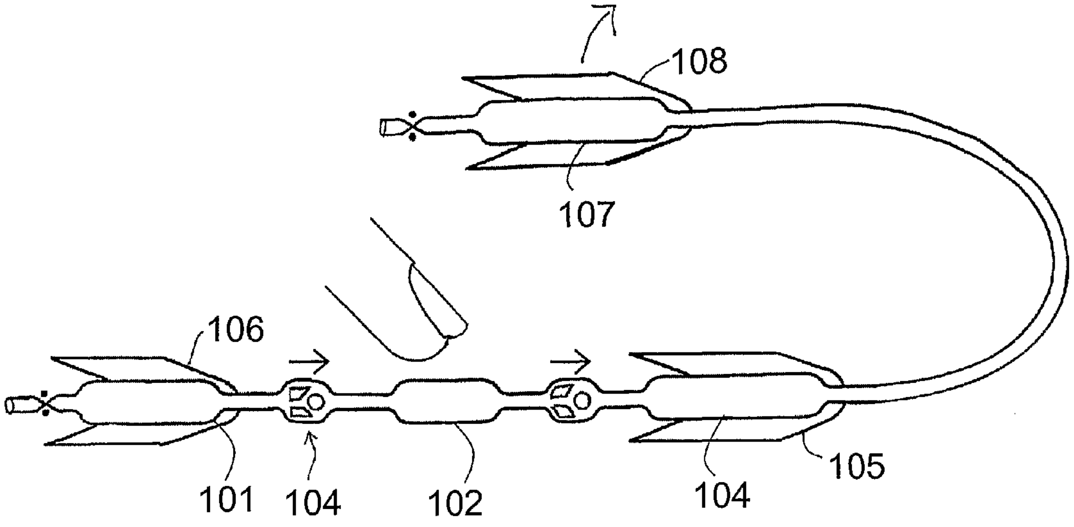
FIG. 10 is a view of a fluid transmission according to another embodiment of the present invention.

FIG. 10 is a view of a fluid transmission 100 according to still another embodiment of the invention, which is similar to that of FIG. 9 but with a further one-way valve and a fluid reservoir. This allows multiple pump stroke actuation, which could be desirable for certain applications.

Referring to FIG. 10, a fluid reservoir 101 in the form of an expanded bag section of unshrunken heat shrink is connected to the driver bag 102 via one-way valve 103. Pressure on driver bag 102 pumps fluid through to the pressure maintaining further driven bag 104 with spring 105. A spring 106 compresses the fluid in reservoir 101 and ensures that driver bag 102 is refilled for the next stroke. For the successful operation of ultimate driven bag 107 and spring 108, the sequence of spring strengths (more accurately spring constant/bag length) is graduated such that spring 105 is stronger than spring 108, which is stronger than spring 106. Driver bag 102 is provided either without a spring (as illustrated) or, optionally, with a spring weaker than all other springs 105, 106, 108.

Hydrostatic pressure has not been found to be important in tests carried out to date, but could conceivably need to be taken into consideration in some applications.

Figure 11:
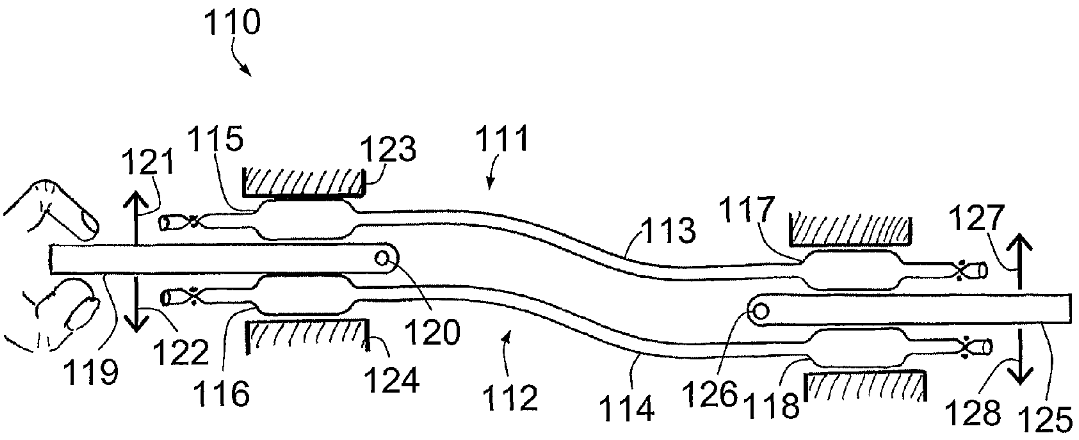
FIG. 11 is a view of a double acting fluid transmission according to another embodiment of the present invention.

FIG. 11 is a view of a double acting fluid transmission 110 according to an embodiment of the invention. This transmission can provide greater force in each stroke direction than single driver bag transmissions acting against a spring return. Fluid transmission 110 includes two conduits 111, 112 of heat shrink polymer tubing, each with shrunken portions (tubes 113, 114 respectively), unshrunken driver bags (115, 116 respectively) and unshrunken driven bags (117, 118 respectively).

The driver bags 115, 116 are located on opposite sides of a lever 119 provided to facilitate manual operation and pivoted at 120. Motion of the lever 119 in direction 121 or 122 squeezes driver bag 115 or 116 respectively against stationary support structure 123 or stationary support structure 124 respectively.

The excess fluid resulting from the compression of either driver bag 115 or driver bag 116 flows along tube 113 or 114 respectively into driven bag 117 or 118 respectively. This causes movement of lever 125 (pivoted at 126) in either direction 127 or 128 respectively. Stationary support structures 129, 130 are provided adjacent to respective driven bags 117, 118 on the remote side in each case of lever 125 to stop the driven bags 117, 118 expanding in an unwanted direction.

In such a system the forward and reverse movements have a symmetrical feel which makes this system suited for a joystick control. A more complex joystick control could employ two further hydraulic bags in a plane perpendicular to that shown in FIG. 11.

Figure 12A:
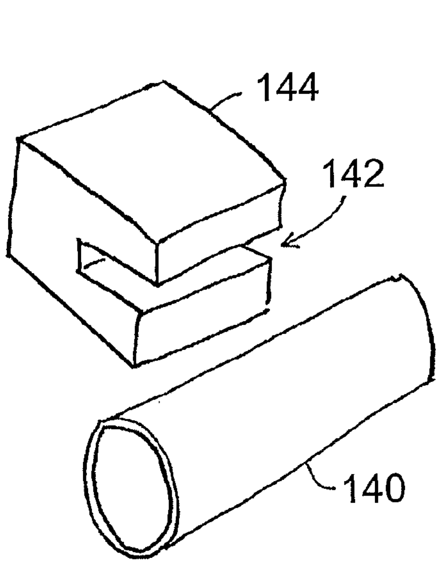
FIGS. 12*a*, 12*b*, 12*c* and 12*d* are successive views of a fluid transmission manufacturing process according to an embodiment of the present invention.
Figure 12B:
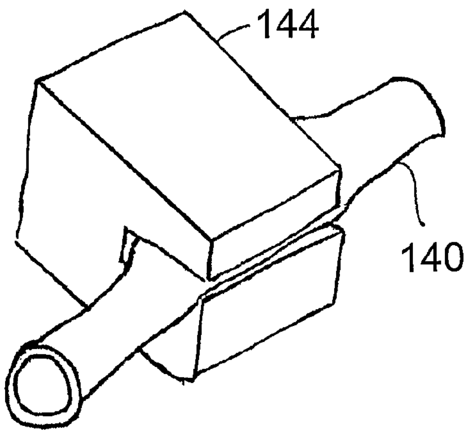
Figure 12C:
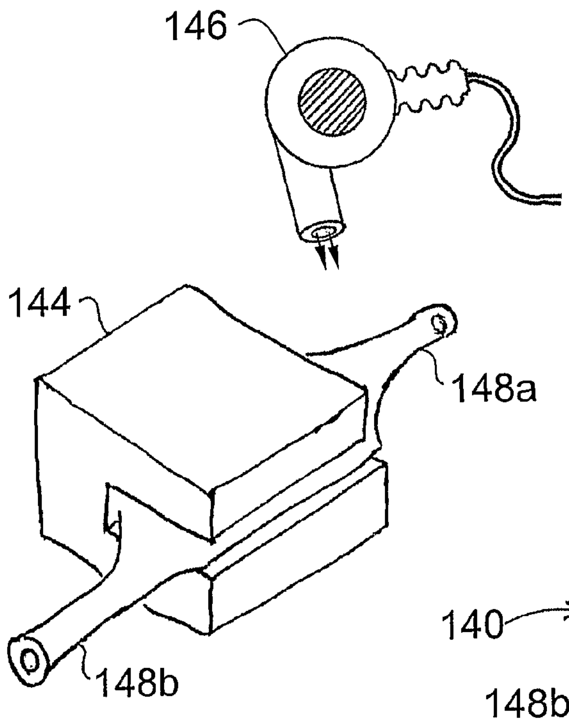

Another embodiment of the invention provides a convenient fluid transmission manufacturing method. Heat shrink tubing is readily flattened out; a convenient method of forming unshrunk sections, therefore, is to flatten the required section(s) of the tubing and place these flattened sections into one or more slots of appropriate length. Referring to FIG. 12*a*, a portion of heat shrink polymer tubing 140 is located in a slot 142 in a work piece 144. FIG. 12*b* is a view of the tubing 140 located in the slot 142. FIG. 12*c* is a view of the tubing 140 located in the slot 142 while the tubing 140 is heated by means of heat gun 146. The slot 142 shields the portion of tubing in the slot 142 from the hot air from the heat gun 146 (or other heat source) being used to shrink the exposed portions 148*a*, 148*b*. Hence, the portion in the slot 142 remain unshrunken.

Figure 12D:
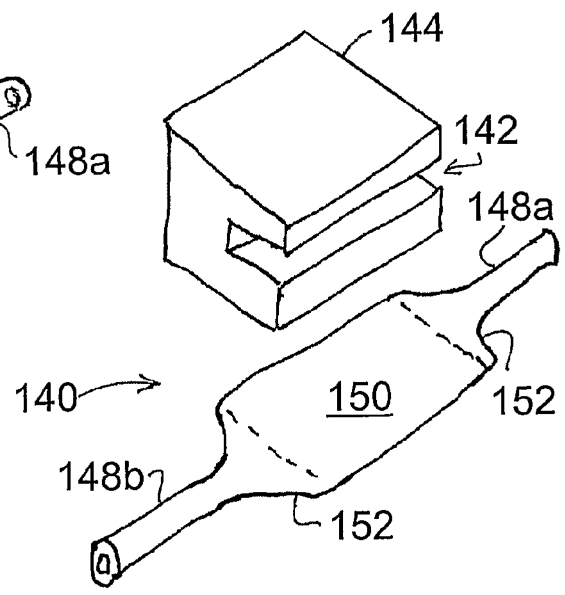

Referring to FIG. 12*d*, once the tubing 140 has been removed from the slot 142, the transition between the circular shrunken portions 148*a*, 148*b* and the flat unshrunken central portion 150 causes the central portion 150 to be thermally set in a form comparable to that of a hot water bottle, where the main body of the central portion 150 is held flat by the shoulders 152 formed at the junction with the shrunken portions 148*a*, 148*b*. This shape is particularly convenient for the design and the installation of the hydraulic member or "loom" in devices in which it is to be used.

It is also possible to shield a portion of heat shrink polymer tubing from being shrunken by gripping that portion with a pair of articulating jaws such as those of a pair of pliers. The method is readily applicable to small volume production or to large scale manufacture.

The shrunken sections outside the slot or jaws generally assume a circular cross section with increased wall thickness. Both these characteristics minimise volume changes in the conducting tube when fluid pressure is increased. Also, while the shrunken section remains hot, it is possible to extend its length by pulling its ends.

It is also possible to arrange the heat shrink polymer tubing in a jig so that, once cooled, the shrunken sections will be set in a way that will make assembly or operation of the ultimate transmission more convenient.

Figure 13:
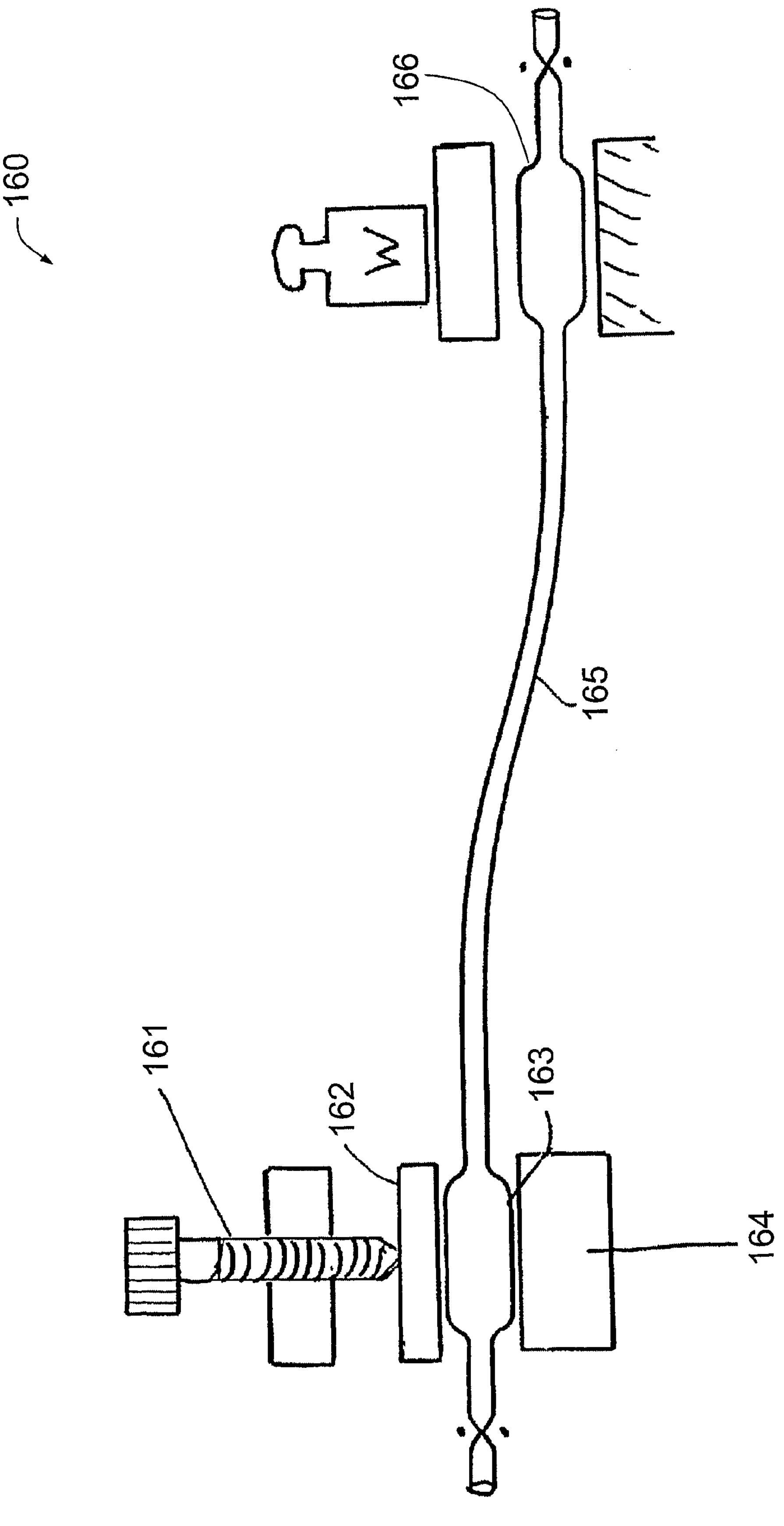
FIG. 13 is a view of a fluid transmission according to another embodiment of the present invention.

FIG. 13 is a view of a fluid transmission 160 according to still another embodiment of the invention, including an adjustment device for adjusting a steady position component. In FIG. 13 rotation of screw 161 produces a motion of plate 162 that compresses a hydraulic driver bag 163 against a fixed plate 164. The fluid displaced moves along shrunken tube section 165 into driven bag 166 and makes it expand. This transmission could be of value where precise adjustment of static loads is required in applications such as micromanipulators, micro-dissectors, tilt adjusters microscope stage focussing and levelling of objects.

Figure 14:
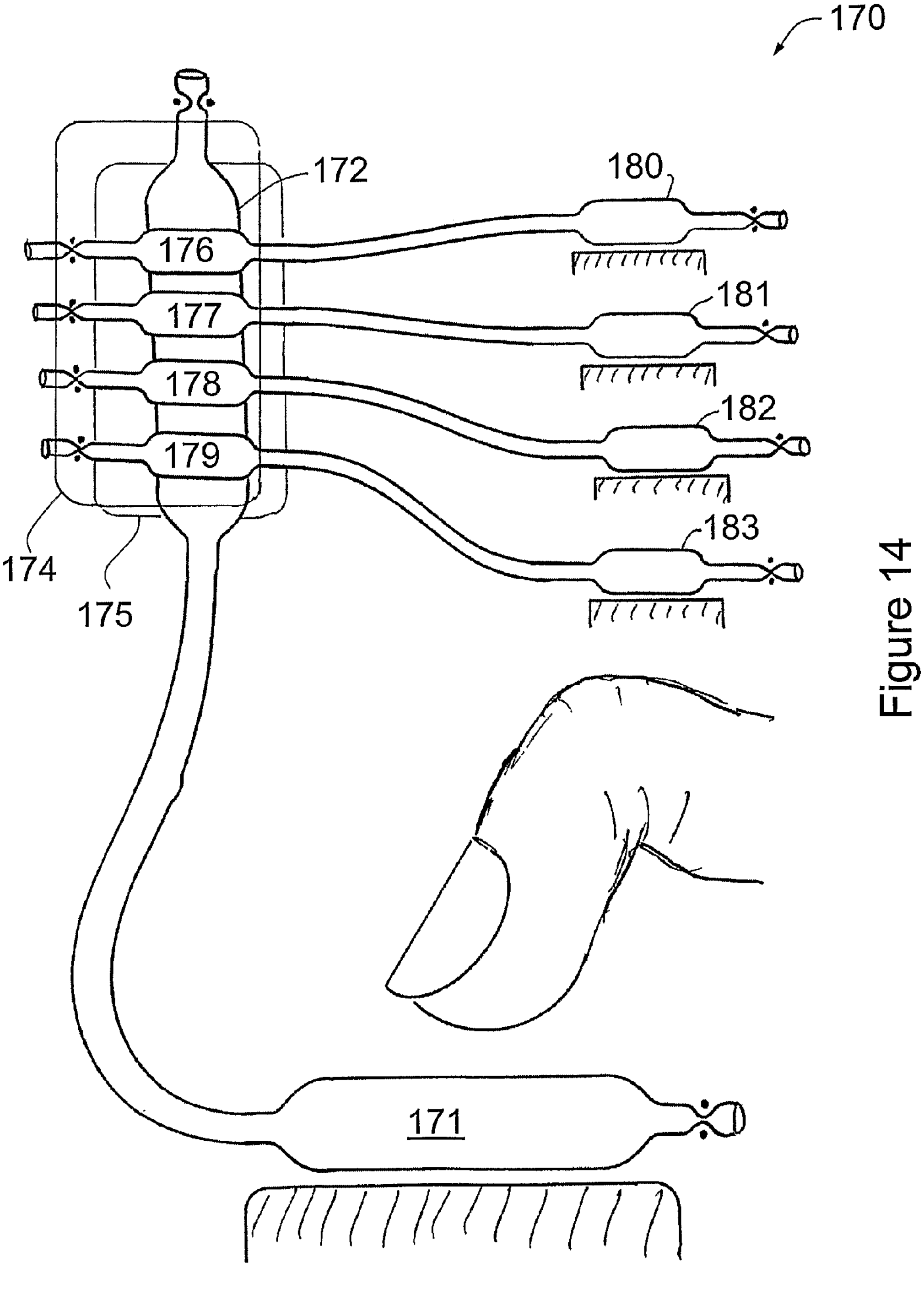
FIG. 14 is a view of a device employing a fluid transmission according to another embodiment of the present invention.

Another device employing a fluid transmission according to an embodiment of the invention is shown generally at 170 in FIG. 14. In device 170, compression of driver bag 171 produces expansion of large driven bag 172 in a volume 173 defined by opposed plates 174 and 175. A number of other secondary driven bags 176, 177, 178 and 179 are also disposed in the volume defined by plates 174 and 175, between large driven bag 172 and one of the plates 174. The expansion of the large driven bag 172 compresses the secondary driven bags 176, 177, 178 and 179 causing expansion of the tertiary driven bags 180, 181, 182 and 183.

It may be desired to operate these tertiary driven bags sequentially using graded springs. If, however, it is intended for them to operate simultaneously it may be desirable to interpose a right plate between secondary driven bags 176, 177, 178 and 179 and the large driven bag 172.

Figure 15A:
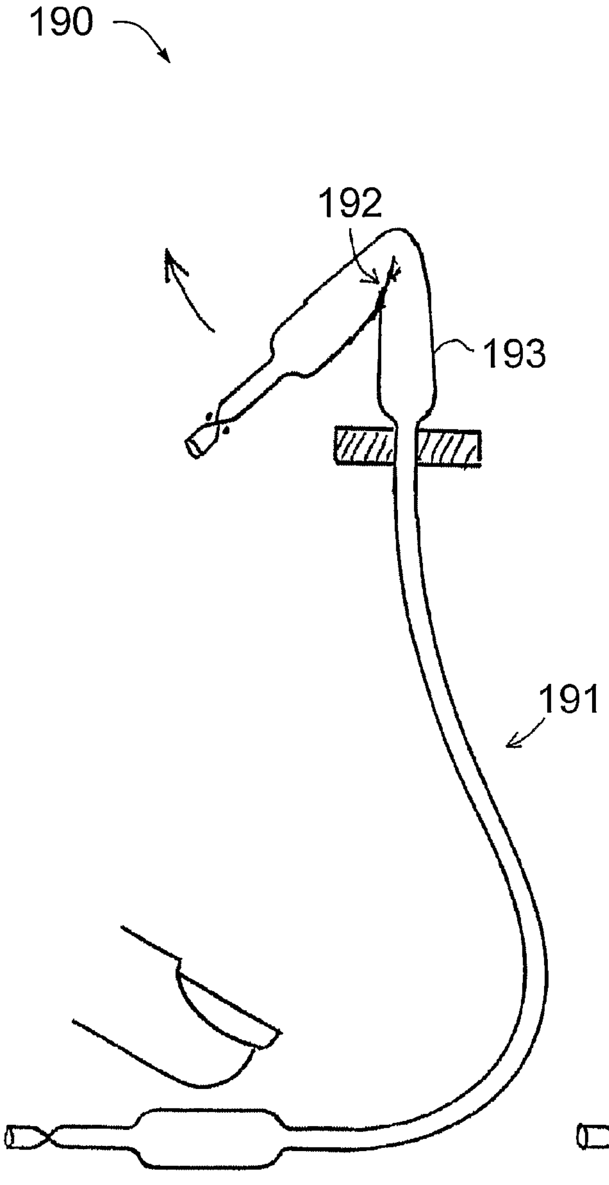
FIGS. 15*a* and 15*b* are views of a system for providing large amplitude motion according to another embodiment of the present invention.
Figure 15B:
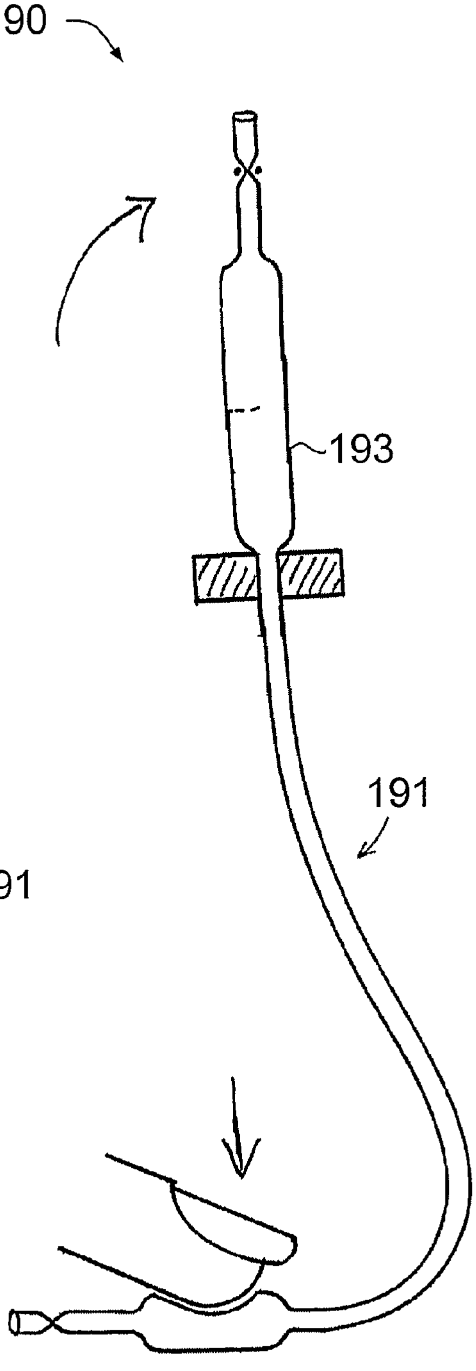

Large amplitude motions can be achieved by systems using the bending of an unshrunken section of the heat shrink tubing. FIGS. 15*a* and 15*b* are views of a system 190 according to another embodiment of the invention, that includes a fluid transmission 191 and in which 140° of movement is obtained by providing a crease line or fold 192 in driven bag 193 (arranged vertically). When fluid enters driven bag 193, the bag opens out from the bent configuration shown in FIG. 15*a* to the straightened configuration shown in FIG. 15*b*.

EXAMPLE

Experiments were carried out with standard 2 mm diameter heat shrink. A driven bag of dimensions 2.5 mm×8 mm was used to lift a mass of 2 kg, raising it by over 1 mm.

A more precise set of experiments was carried out using Zeus Sub-Lite-Wall brand PTFE Heat Shrinkable tubing. (PTFE heat shrink tubing remains highly flexible even when shrunk, and can have an external diameter of as little as ~125 μm when shrunk, so is particularly advantageous in the embodiments described herein.) A driven bag was formed from this material which had the dimensions 0.9 mm×3.0 mm. The driven bag lifted a mass of 120 g to a height of approximately 0.5 mm. The wall thickness of this tube is given by the manufacturer as 0.051 mm. This means that the stroke of this motion is 5 times the collapsed wall thickness, which is very large compared with other miniature actuators such as piezo elements and the like.

The driven bag was tested with excess pressure to destruction. The irreversible stretching and bursting pressure of the unsupported bag was found to be in the region of 40 to 60 kPa.

If the driven bag were supported, it is estimated that the bag could raise over one kilogram with a stroke of 0.2 to 0.3 mm.

A variety of heat shrink tubing has been successfully used to construct hydraulic systems according to the present invention, including:

i) Zeus brand PTFE heat shrink 4:1, in a wide range of tube sizes;

ii) Sumitomo Corporation "Sumitube C" brand polyolefin tube (which has a shrink temperature of 90° C.), in several sizes and in both clear and pigmented varieties;

iii) Flame retardant polyolefin; and iv) Tyco Raychem brand PVC heat shrink tube.

As an alternative to heat shrink, the systems of the present invention may also be constructed with blow expanded tubing. Zeus brand PTFE tube was successfully expanded and tested. Further, it is envisaged that blow moulding could also be used to construct the bags and tubing. Though not tested, it is envisaged that a wide range of thermoplastics would be suitable, if generally less convenient than heat shrink.

Figure 16A:
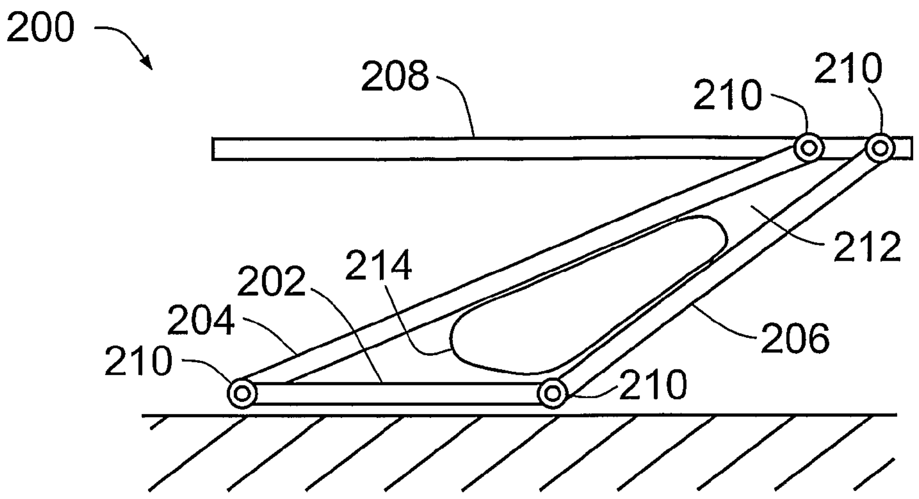
FIGS. 16A and 16B are schematic views of a trapezoidal actuator device according to another embodiment of the present invention.
Figure 16B:
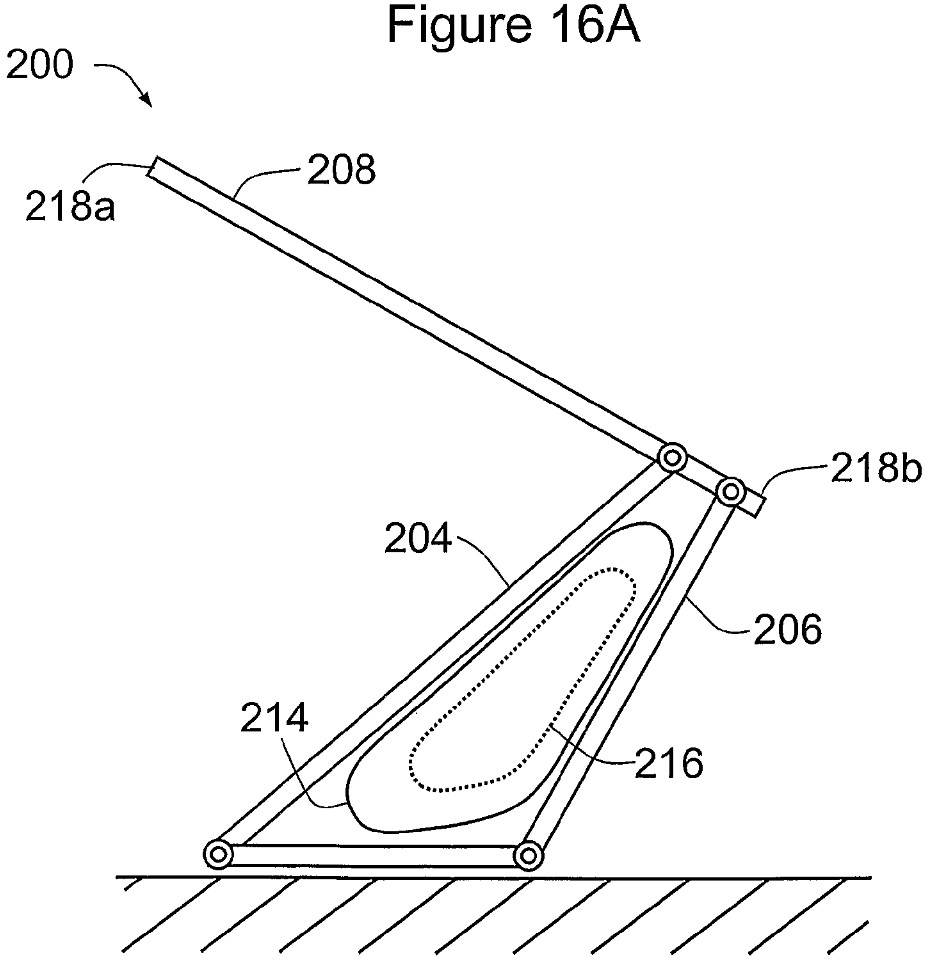

Another type of device employing a fluid transmission according to an embodiment of the invention is shown schematically at 200 in FIGS. 16A and 16B. The device 200—which constitutes an actuator—comprises four straight, essentially rigid members 202, 204, 206, 208 that are pivotably coupled to one another by four pins 210 and define a trapezoidal shaped space 212. The pins that couple the base member 202 to side members 204, 204 are spaced more widely than the pins that couple the side members 204, 204 to top member 208. In addition, top member 208—though terminating at the point at which it is coupled to one side member 206, extends beyond side member 204.

The device includes, within trapezoidal shaped space 212, a driven bag 214 (coupled by a conduit for admitting a fluid, which conduit is—for simplicity—omitted from these figures).

When a fluid is driven into the driven bag 214 (whether by a driver bag of the type described above or otherwise), driven bag 214 expands to a greater volume, as depicted in FIG. 16B. (For the purposes of comparison, the initial shape and volume of driven bag 214 is shown with dotted curve 216.) The expansion of driven bag 214 forces side members 204, 206 upwards. In addition, owing to the closer spacing of the pins coupling these side members to the top member 208, the top member 208—though initially parallel to base member 202, is progressively rotated until one end 218*a* is considerably higher than the other 218*b*.

The device 200 thus acts as a hydraulic actuator. As will be appreciated, in a practical device the members may be in the form of plates and the pins may be replaced with any other suitable coupling mechanism, including hinges, magnets, flexible members (such as nylon thread), ball/socket joints, and combinations of these.

Figure 17A:
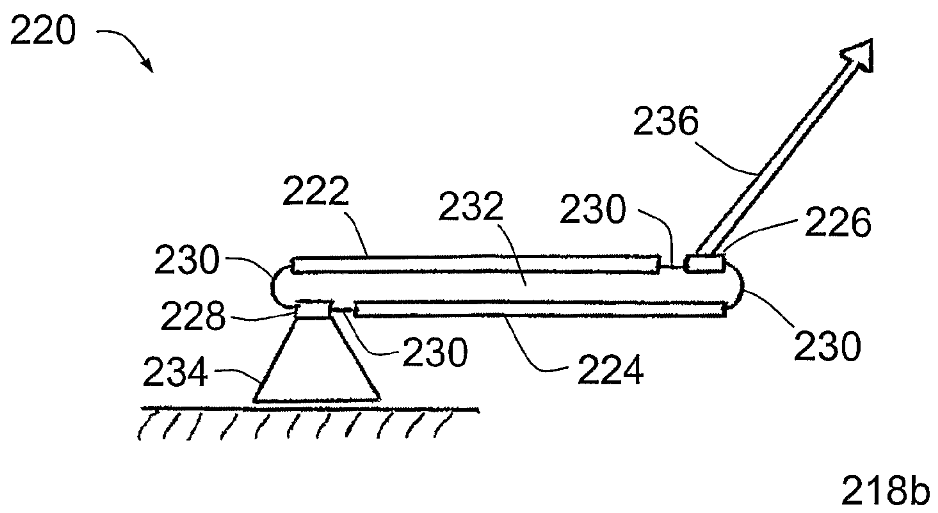
FIGS. 17A and 17B are schematic views of a parallelogram actuator device according to another embodiment of the present invention.
Figure 17B:
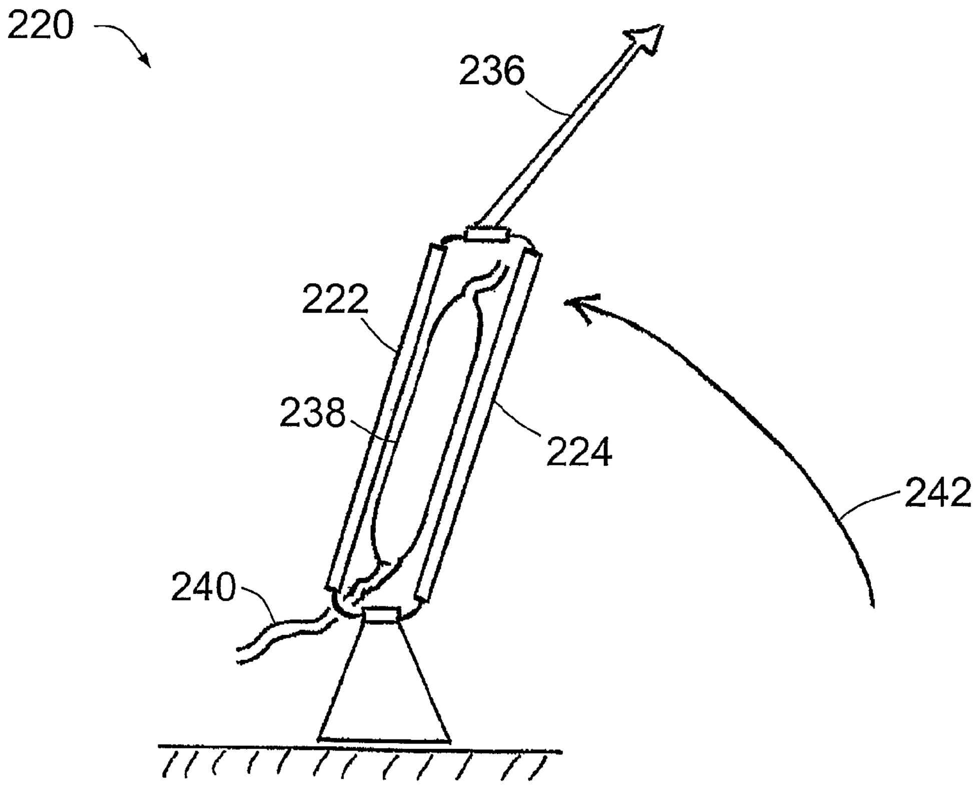

A device 220 comparable to that of FIGS. 16A and 16B according to another embodiment is shown schematically in FIGS. 17A and 17B. Referring to FIG. 17A, device 220 comprises four rigid members 222, 224, 226, 228, in this embodiment coupled by four flexible hinges 230 to form an enclosure 232 for a hydraulic driven bag (not shown).

Base rigid member 228 is coupled to a fixed base 234, while one or more of the other rigid members (in this example, load member 226) is connected to whatever load 236 that it is desired be moved.

FIG. 17B shows device 220 after hydraulic driven bag 238 has been inflated through tube 240. This causes that member 226 most remote from base member 228, as well as the load 236, to move upwardly in an arc 242. The enclosure 232 defined by rigid members 222, 224, 226, 228 is now parallelogram in shape.

Figure 18A:
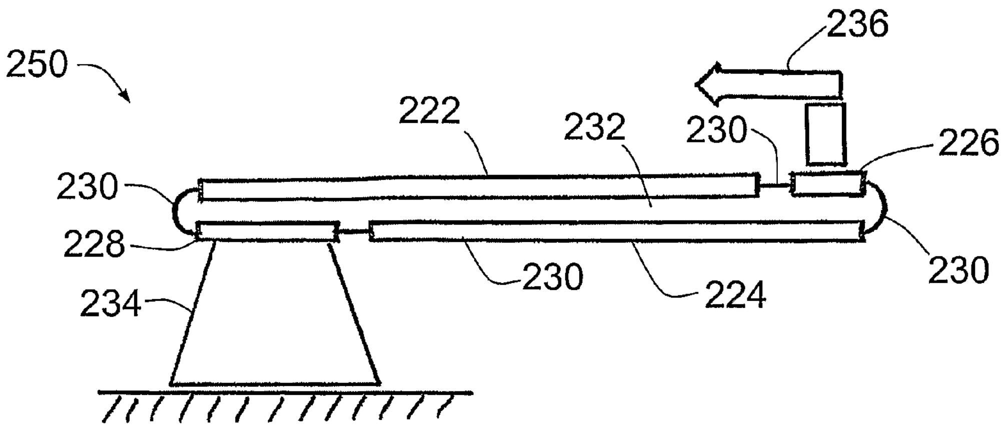
FIGS. 18A and 18B are schematic views of a flatpack actuator device according to another embodiment of the present invention.
Figure 18B:
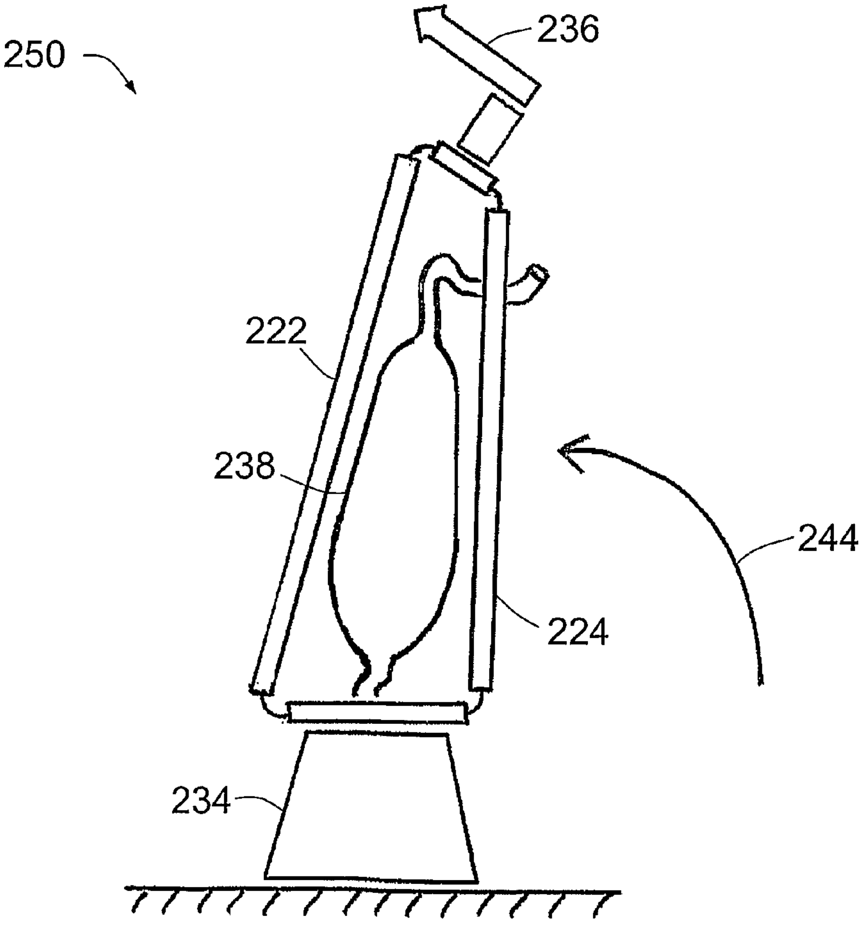

Another embodiment comparable to device 220 of FIGS. 17A and 17A is shown schematically at 250 in FIG. 18A and 18B, and like reference numerals have been used to indicate like features. As in device 220, the combined lengths of members 228 and 224 equals that of members 222 and 226 (referred to herein as the "flatpack" criterion), but base member 228 is longer than load member 226 and member 230 is correspondingly shorter than member 222.

Accordingly, when driven bag 238 is expanded, load 236 is rotated relative to the base 234, as well as being moved through arc 244.

Figure 19:
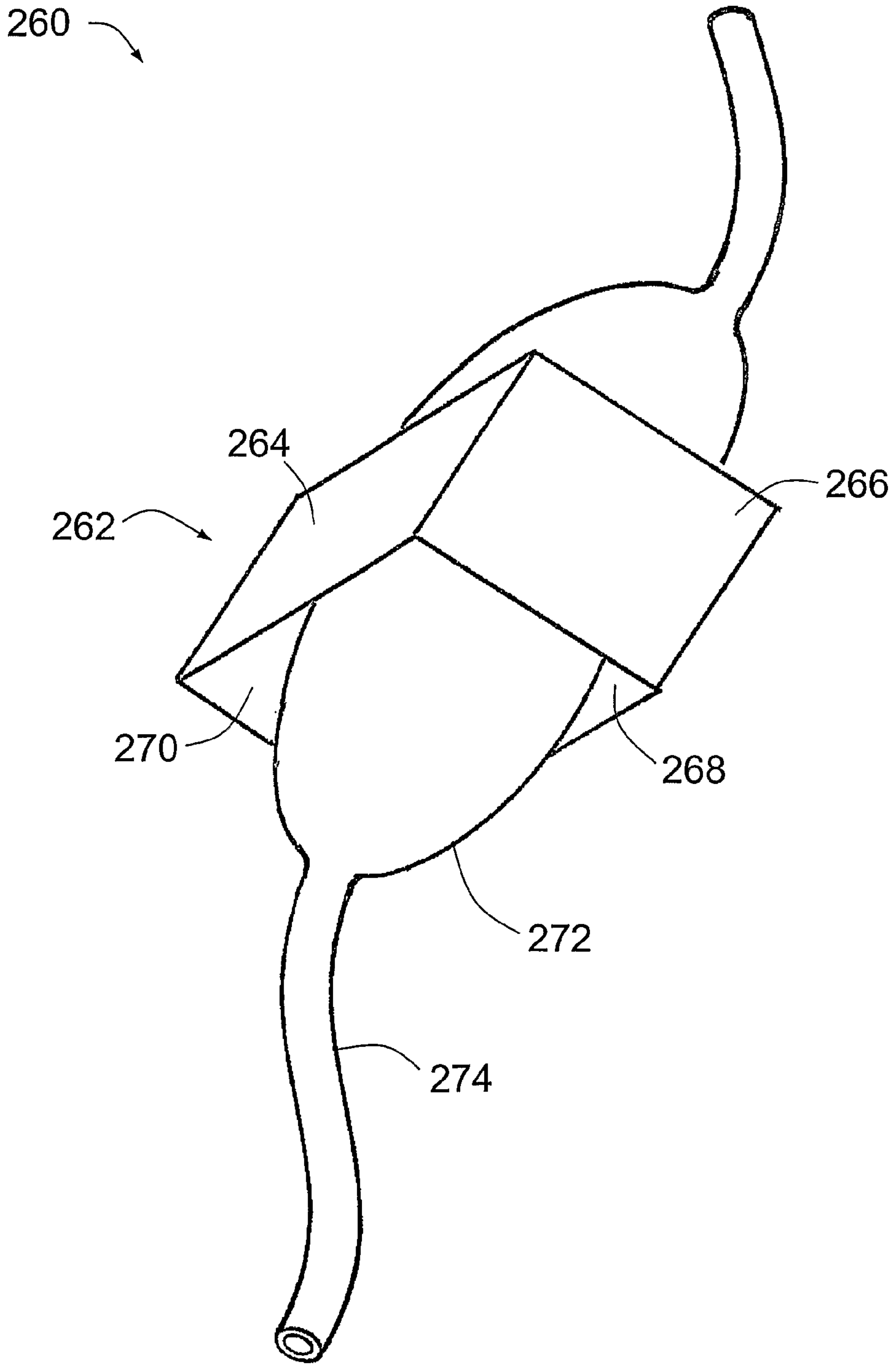
FIG. 19 is an isometric view of a rhomboid actuator device according to another embodiment of the present invention.

FIG. 19 is an isometric view of a hydraulic unit 260 according to another embodiment, comprising a rhombus 262 with four sides 264, 266, 268, 270 of equal size, with adjacent sides joined by respective hinges (not shown). The rhombus 262 defines an interior volume in which a hydraulic bag 272 is located oriented transverse to the rhombus 262. When a fluid is driven into hydraulic bag 272 through tube 274, hydraulic bag 272 and hence rhombus 262 is expanded in the manner illustrated in FIG. 17B.

Figure 20:
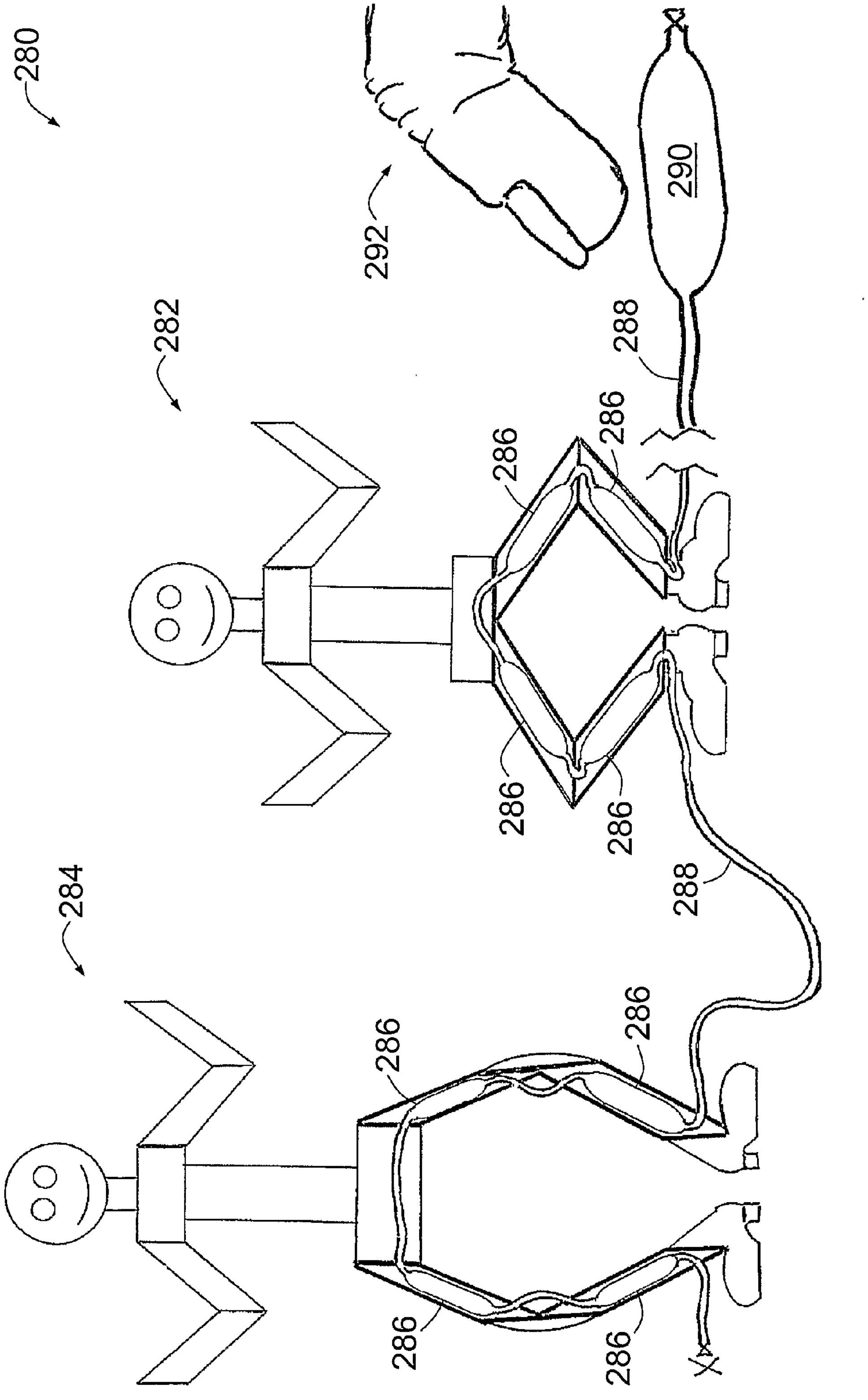
FIG. 20 is schematic view of a tableaux of moveable manikins according to another embodiment of the present invention.

The hydraulically actuated devices of FIGS. 16A to 19 have numerous applications. One example is shown schematically in FIG. 20, which depicts a tableaux 280 of moveable manikins 282, 284. Each FIG. 282, 284 has legs comprising pairs of parallelogram-shaped segments, those of manikin 282 reversed relative to those of manikin 284; each segment encloses a hydraulically driven bag 286. The bags 286 are coupled in series by tube 288 to a driver bag 290. The depression of the driver bag 290 by a finger 292 forces fluid along tube 288 into the ankle of manikin 282 and into the bags 286. The bags 286 of manikin 282 expand and activate the parallelogram-shaped segments, causing manikin 282 to bob up. The fluid continues to move along tube 288 and enters the ankle of manikin 284, expanding the bags in that manikin. This activates the parallelogram-shaped segments of manikin 284, which causes manikin 284 to bob down.

Figure 21:
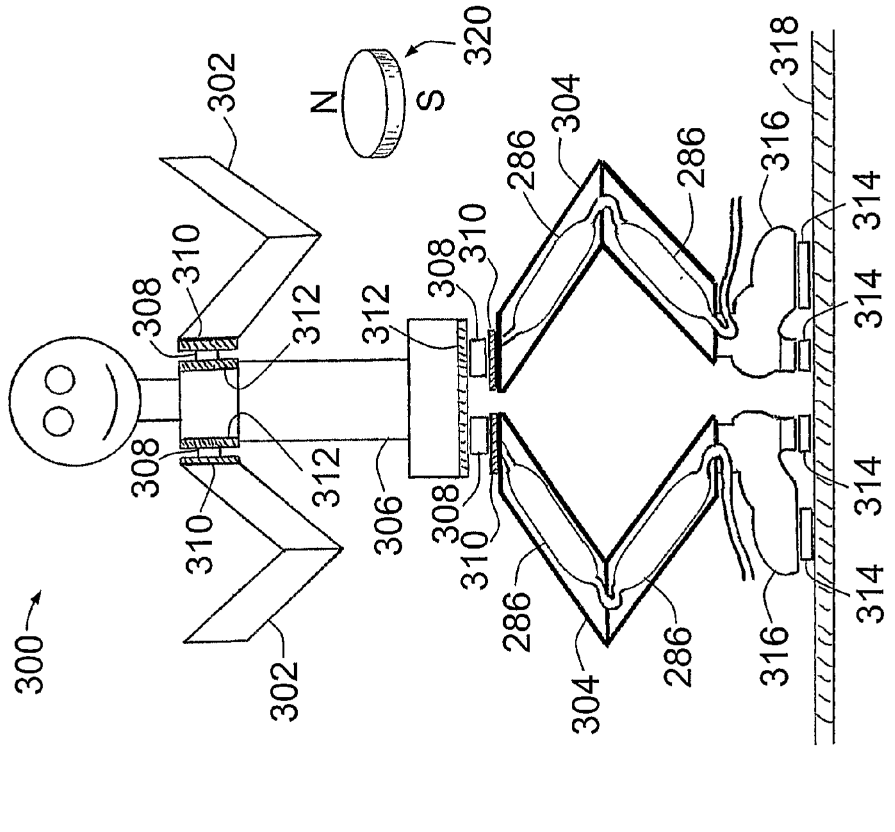
FIG. 21 is schematic view of a doll according to another embodiment of the present invention.

FIG. 21 is a schematic view of a hydraulically actuated manikin or doll 300 according to another embodiment. Doll 300 is similar to manikin 282 of FIG. 20 (and like reference numerals have been used to indicate like features), but its upper and lower limbs 302, 304 are attached to the trunk 306 of the doll 300 by magnets 308. This allows an increased range of static poses of the doll 300. Limbs 302, 304 are tipped with small pieces of iron 310, and the trunk 306 has complementary pieces of iron 312; magnets 308 attract the respective pieces of iron to hold the limbs 302, 304 to the trunk 306. Alternatively, each magnet 308 may attract a piece of iron on one side of each joint and be glued to the other. Doll 300 has further magnets 314 on the soles of the shoes 316 of the doll 300, for attracting the feet of the doll 300 to a magnetic floor 318. Suitable strong compact rare earth magnets are available in disc form, as depicted (enlarged) at 320.

Figure 22:
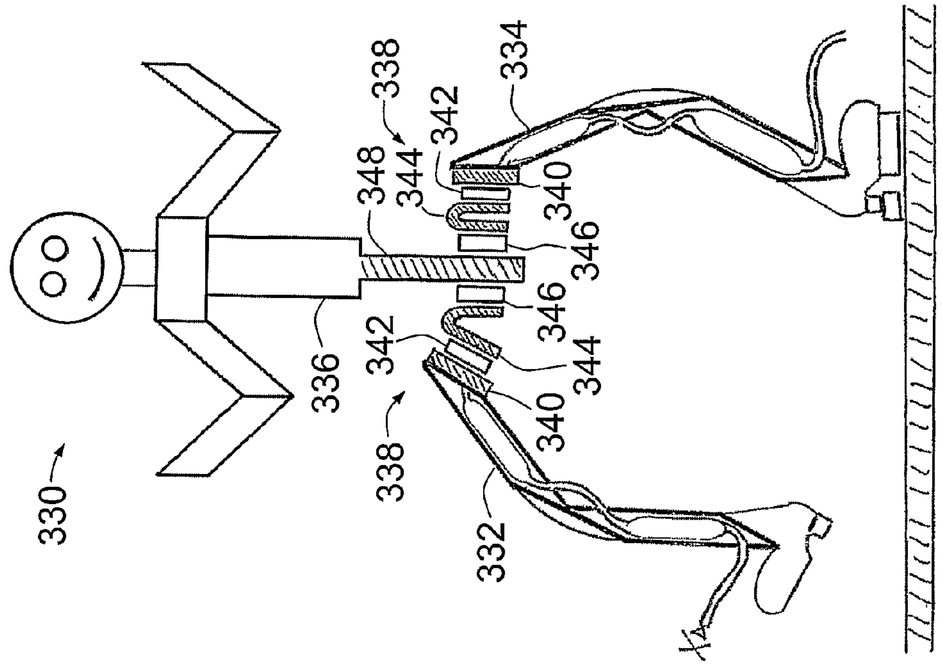
FIG. 22 is schematic view of a doll according to another embodiment of the present invention.

FIG. 22 is a schematic view of a hydraulically actuated manikin or doll 330, according to another embodiment, which a further degree of freedom of static pose is provided. This is done by including U shaped pieces of soft iron sheet between separate active units or between other components where an articulated joint is desired. Referring to FIG. 22, the legs 332, 334 of doll 330 are articulated to trunk 336 of doll 330. At each hip joint 338, a piece of flat iron 340 is attached to the top of the leg and held tight by a flat magnet 342. The other side of magnet 342 holds fast to a U shaped piece of soft iron 344. Iron 344 (formed by folding a flat piece into a U shape) is shown edge-on. The other side of the U shaped piece of iron 344 is held by a further magnet 346, whose other pole holds fast to a lower iron portion 348 of trunk 336. The two pieces of iron 344 are generally identical, except that one (on the left in the figure) is close in shape to a V. These pieces of iron 344 can also be rotated to give a full range of static ball joint positions.

Figure 23:
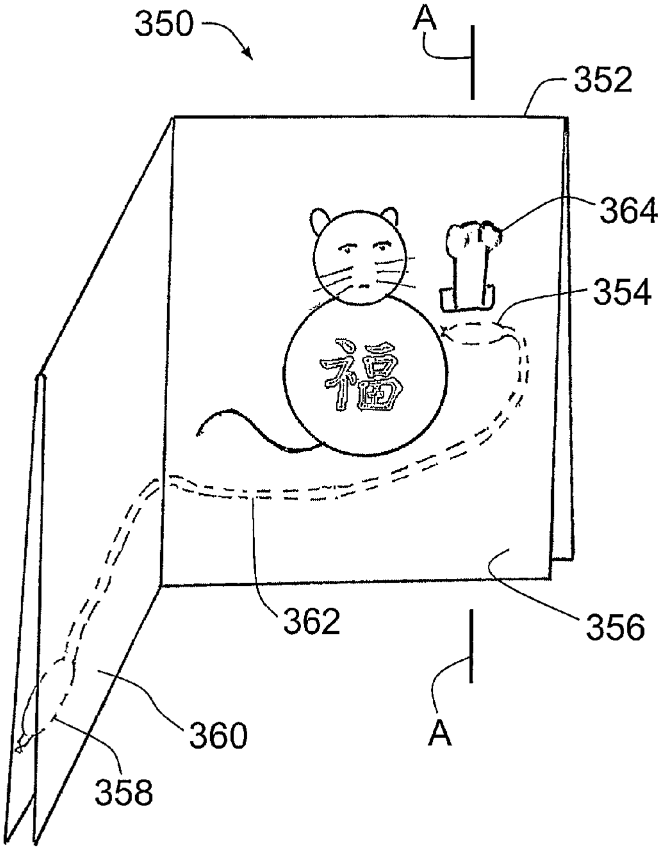
FIG. 23 is a view of novelty greeting card according to another embodiment of the present invention.

FIG. 23 is a view of another embodiment, a greeting or good luck card 350. Card 350 has a fold 352 at its upper edge, and includes a concealed actuated bladder 354 behind the face 356 that is exposed once the card has been opened (as depicted in this figure). An actuator bladder 358 is located behind the opposite face 360 and connected to the first bladder 354 by tube 362. Pressure on actuator bladder 358 by the hand of the recipient of the card 350 causes a fluid held within the bladders and tube to be forced out of the actuator bladder and into actuated bladder 354; actuated bladder 354 is coupled to a exposed, cardboard movable part 364 of face 356 (in this example, a hinged paw of a cat design), such that the expansion of actuated bladder 354 causes movable part 364 to move.

Figure 24:
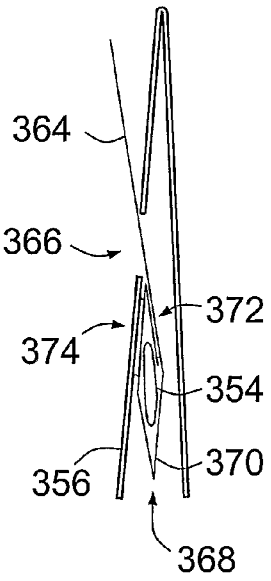
FIG. 24 is a cross-sectional view of the novelty greeting card of FIG. 23.

FIG. 24 is a cross-sectional view—not to scale—of card 350 (along line A-A in FIG. 23). Card 350 has a slot 366 through which the movable part 364 projects. The lower, concealed portion 368 of movable part 364 is folded into a parallelogram 370 with paper hinges at each vertex (not shown). Parallelogram 370 is glued at 372 to itself, and at 374 to the rear of face 356. Actuated bladder 354 is located inside parallelogram 370.

Figure 25:
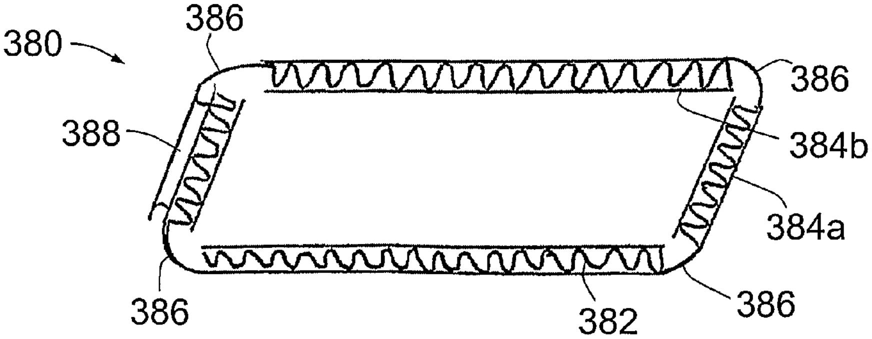
FIG. 25 is a cross-sectional view of an actuator parallelogram according to another embodiment of the present invention.

The parallelograms and trapezoids of the devices described above may be constructed of many materials, including many that are inexpensive such as paper and cardboard. For example, FIG. 25 is a cross-sectional view of an actuator parallelogram 380 formed from a piece of Kraft paper (comprising corrugated cardboard 382 between paper skins 384*a*, 384*b*). The external skin 384*a* forms the hinges 386. The integrity of the parallelogram 380 is maintained by gluing at 388.

Figure 26A:
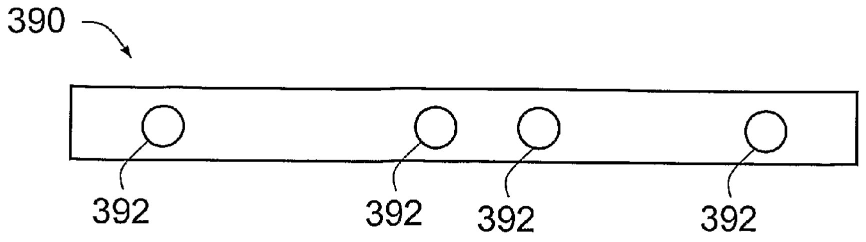
FIGS. 26A and 26B are schematic views illustrating the manufacture of an actuator device according to another embodiment of the present invention.
Figure 26B:
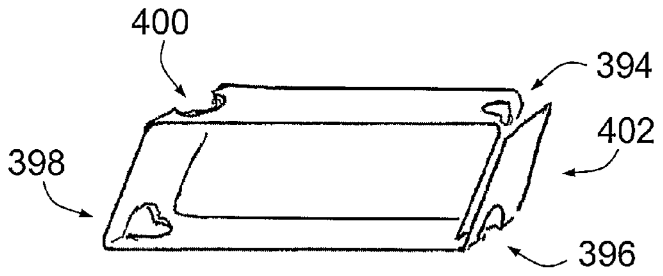

FIG. 26A depicts an alternative approach, comprising a strip 390 of metal, plastic, paper or cardboard. The strip 390 has four holes 392, and is formed into a parallelogram (as shown in FIG. 26B) by being bent at these holes. The material at the sides of the holes provides the hinges at 394, 396, 398, 400. The ends of strip 390 are glued or otherwise fastened together at 402.

Figure 27A:
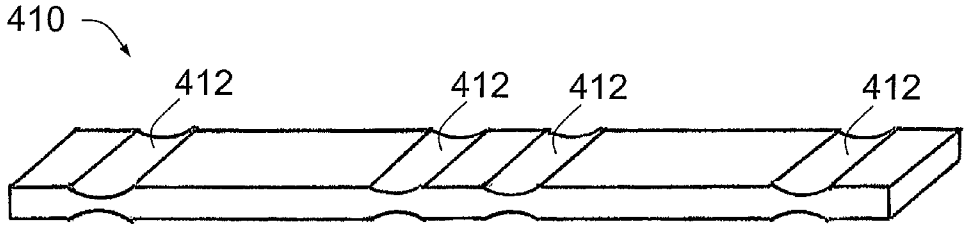
FIGS. 27A and 27B are schematic views illustrating the manufacture of another actuator device according to another embodiment of the present invention.
Figure 27B:
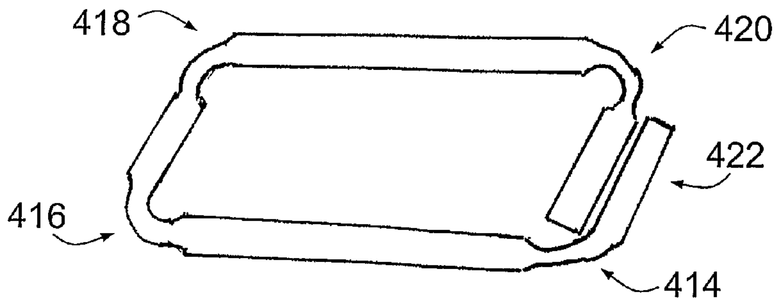

FIG. 27A depicts a still further approach, comprising a strip 410—again of metal, plastic, paper or cardboard—in which sections 412 have been weakened by abrasion or erosion so that the strip 410 can be bent into a parallelogram 414. The weakened abraded or eroded sections 412 provide the hinges 414, 416, 418, 420. The ends of strip 410 are fastened at 422.

Figure 28A:
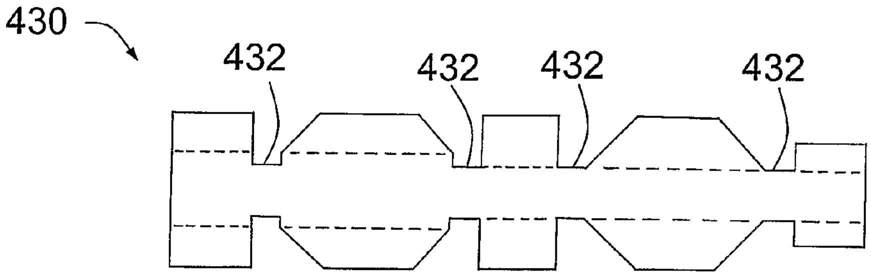
FIGS. 28A to 28D are schematic views illustrating the manufacture of still another actuator device according to another embodiment of the present invention.
Figure 28B:
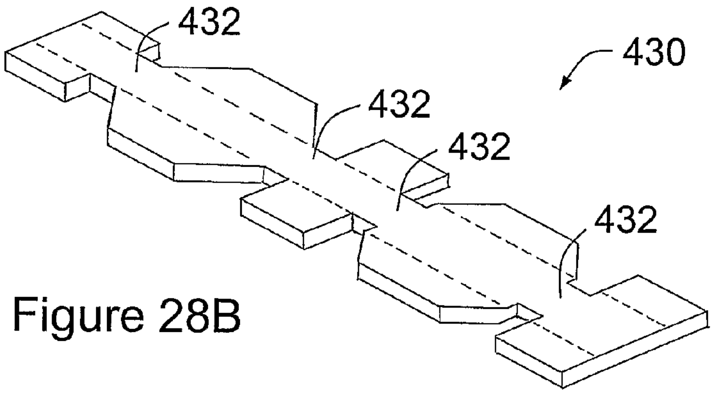
Figure 28C:
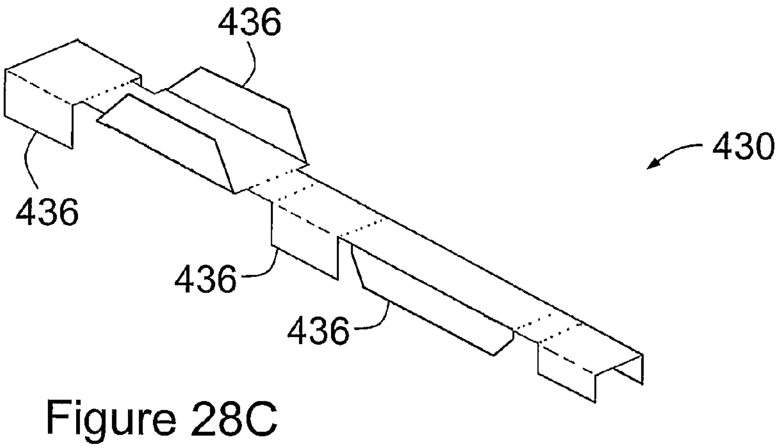

FIGS. 28A, 28B, 28C and 28D are successive views of the fabrication of a parallelogram 430 according to still another embodiment, and formed by stamping and folding a sheet 432 of material such as sheet metal. Referring to the plan and perspective views of FIGS. 28A and 28B, four neck portions 434 are provided to act, ultimately, as hinges. Referring to FIG. 28C, side tabs 436 of sheet 432 are folded upwardly and downwardly respectively.

Figure 28D:
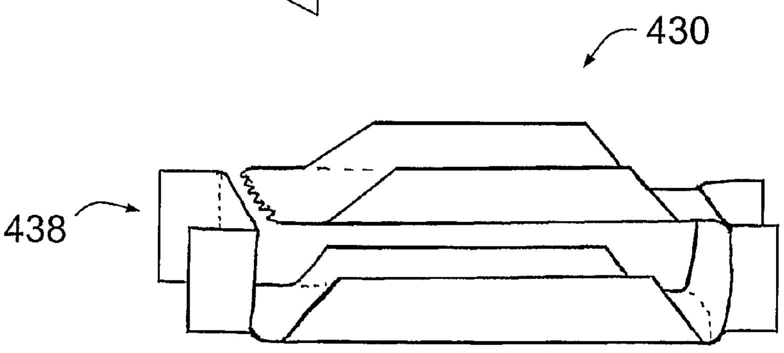

The final, folded configuration is shown in FIGS. 28D (with one end portion, which would be fastened to the other end portion 438, omitted for clarity).

The embodiments of FIGS. 16A to 28D may also optionally include a mechanism for providing a restoring force to urge the bladder—after actuation—back to a collapsed condition and ready for re-activation. This may be done in a number of ways.

For example, the hinges may be made of resilient metal strip bent to shape at the appropriate positions to form a flattened parallelogram. This may conveniently be achieved by making the entire perimeter of the parallelogram from one single piece of resilient strip and attaching rigid pieces to the strip at appropriate sections to form the unbending sides of the parallelogram.

Alternatively, a restoring force could be provided by independently positioned pieces of resilient wire that push together opposing sides of the parallelogram. The resilient wire would be of similar shape to the spring used in conventional clothes pegs.

Another approach employs rubber bands. These could be positioned around the parallelogram, acting to restore the flattened position of the parallelogram.

Figure 29:
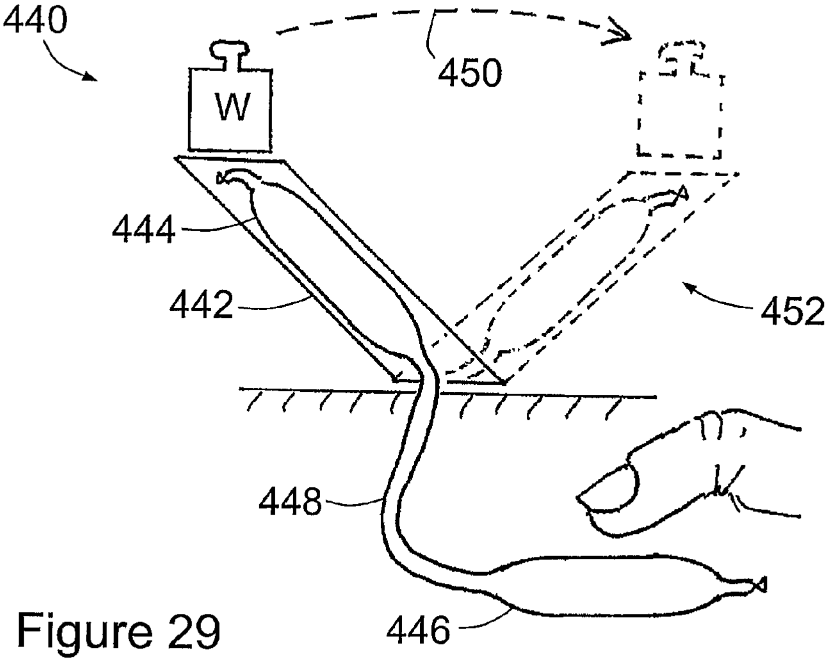
FIG. 29 is a view of a bi-stable actuator according to another embodiment of the present invention.

Still further, the force of gravity could be exploited, acting on a weight. FIG. 29 is a view of such a system 440. The inertia of the weight W is used to cause a parallelogram 442 to act in a flip-flop manner. The system 440 includes a hydraulic mechanism, comprising actuated bladder 444 inside parallelogram 442, actuator bladder 446 and connecting tube 448. When this hydraulic mechanism is operated to produce a fast motion, the inertia of the moving weight W causes the weight W to overshoot, traversing an arc 450 from the initial illustrated position to a new stable, rest position shown dashed at 452. Hence, a bi-stable motion is produced.

Figure 30:
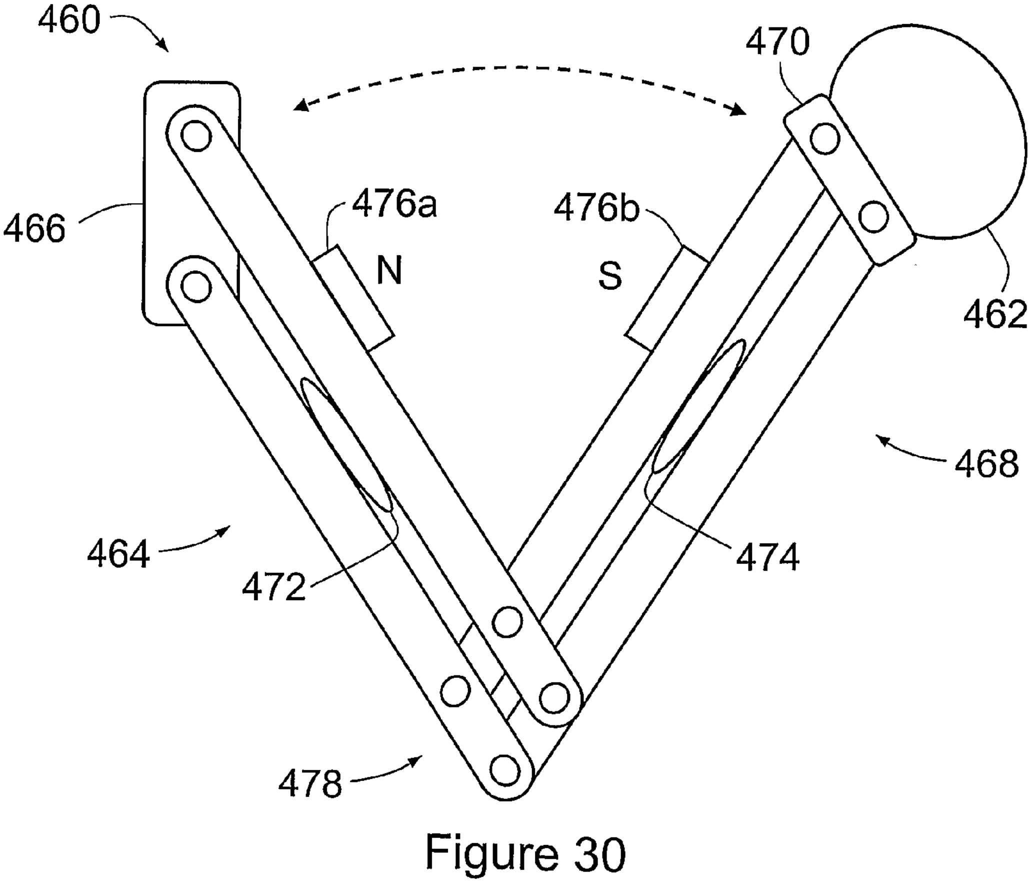
FIG. 30 is a schematic view of an armature provided with an actuator according to a further embodiment of the present invention

FIG. 30 is a schematic view of an armature 460 provided with an actuator according to a further embodiment of the present invention. The armature 460 could be used in many applications, including in load bearing structures, but in the illustrated embodiment it is adapted for use as the arm of a boxer figurine, so is fitted with a miniature boxing glove 462.

Armature 460 principally comprises a pantograph-like framework of pivotally connected rods. A first pair of rods 464 are pivotally connected to a base 466 (attached to or forming the shoulder of the boxer figurine), pivotally connected to second pair of rods 468. The second pair of rods 468 are pivotally coupled to a terminating element 470, to which is attached the boxing glove 462. A first actuated bag 472 is located between first pair of rods 464, and a second actuated bag 474 is located between second pair of rods 468. The armature 460 includes tubing (not shown) for conducting fluid to these bags. When these bags 472, 474 are expanded, the respective pairs of rods are urged apart, which results in the whole armature extending laterally from base 466.

The armature 460 also includes a releasable magnetic latch in the form of permanent magnet **476*a* and piece of iron 476*b*. Magnet 476*a* and iron 476*b* are located opposite each other on the upper rod of each pair of rods 464, 468. In a minimally extended arrangement, magnet 476*a* and iron 476*b* are in contact and latch the armature in that configuration. When the bags 472, 474 are expanded, the armature 460 initially will not respond, as the attraction between magnet 476*a* and iron 476*b* will initially exceed the force of the bags urging the magnet and iron apart. When the force of the bags becomes sufficient to break the attraction, the armature 460 and boxing glove 462** extend rapidly, simulating what in physiology is termed a ballistic movement.

It will be noted that the rods 464, 468 of armature 460 define—at the "elbow" 478—an additional parallelogram. This additional parallelogram does not have a bag in it (though in some embodiments it may), but links the motions of the two parallelograms defined by first rods 464, second rods 468, base 466 and terminating element 470. This is advantageous in some applications, such as where variable loads are encountered.

In one variation on this arrangement a pair of flexible plastic "fridge" magnets is employed. The magnetic poles on such magnets are arranged in a series of parallel lines (viz. N-S-N-S-N etc); if two such magnets are slid against one another (moving at right angles to the pole lines) a jerky periodic motion results, which can make the motion of a doll more realistic and add interest.

Figure 31:
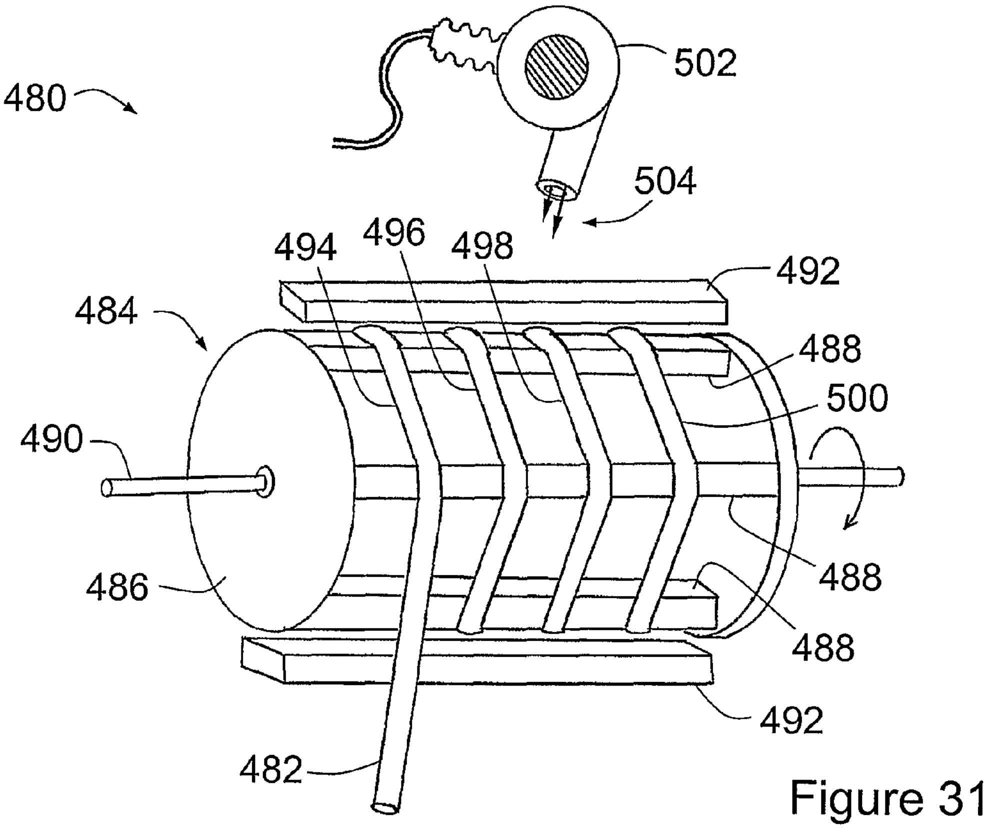
FIG. 31 is a view of a fabrication apparatus according to an embodiment of the present invention for producing heat shrink tube and bags.

The tube/bag combinations of the above-described embodiments can be made by any suitable technique, but certain techniques adapted for mass production are described below. FIG. 31 is a view of one fabrication apparatus 480 for producing heat shrink tube and bags. Apparatus 480 comprises a framework 484 that includes a barrel 486 with flat exterior panels 488 distributed about the barrel 486 to support the tube 482. The barrel is rotatably mounted on a shaft 490. The framework 484 also includes two protective bars 492, which rotate with the barrel 486 and protect portions of heat shrink tube 482 from the hot air used to shrink the tube 482. Protective bars 492 that cooperate with two of the exterior panels 488 to clamp the tube 482, thereby defining unprotected lengths 494, 496, 498, 500 of heat shrink tube 482.

Apparatus 480 also includes a hot air gun 502 for directing hot air 504 towards heat shrink tube 482. The hot air 506 shrinks the unprotected lengths 494, 496, 498, 500 of heat shrink tube 482 to form the non-expandable tube sections of a hydraulic system. The protected sections of the heat-shrink tube 482 form the bladders or bags of that hydraulic system.

Figure 32:
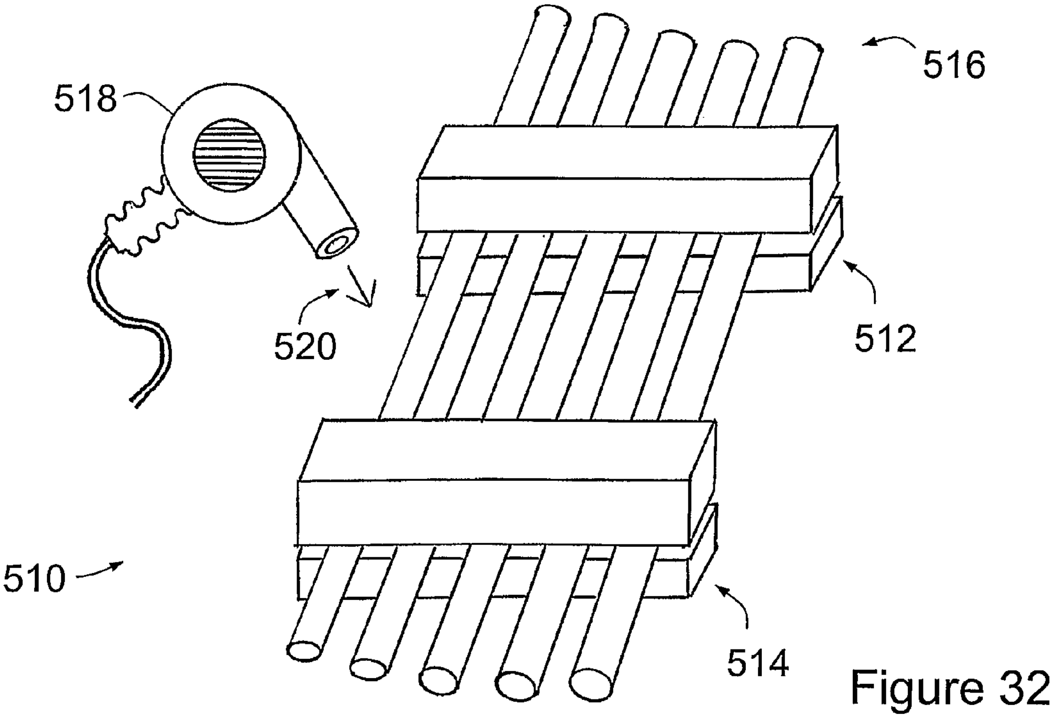
FIG. 32 is a view of a fabrication apparatus according to another embodiment of the present invention for producing heat shrink tube and bags.

FIG. 32 is a view of another fabrication apparatus 510 for producing heat shrink tube and bags. Apparatus 510 comprises two clamps 512, 514 (each comprising a pair of blocks) for retaining five lengths 516 of heat shrink tube. Hot air gun 518 directs hot air 520 towards the lengths 516 of heat shrink tube, shrinking the unprotected portions of lengths 516 to form the non-expandable tube sections of a hydraulic system, but leaving the clamped and hence protected portions of lengths 516 to for the bladders of the hydraulic system.

It can be seen, therefore, that the various embodiments of the present invention provide a wide range of possible actuators for use in many devices, with the actuators constructed of a variety of inexpensive materials and having simple hinges that may be integral with the quadrilateral component. It will also be appreciated that the actuators could be based on other polygons.

Other arrangements, however, comprise an actuated bag located between a pair of hinged elements. Still other actuators employ more than one actuated bag.

Possible applications include, in addition to those described above, the provision of facial movement in dolls and the like, animated books (particularly for children), industrial robotics, lens focussing mechanism (such as for mobile telephone cameras or other digital cameras), other electronic equipment where mechanical and electromechanical actions are employed, slow release lids and covers, micro/nanotechnology devices, and scientific instrumentation (such as microscopy or endoscopy stages).

Conclusion

The miniature fluid transmissions made possible according to the present invention are particularly suited to slow uniform linear motion where substantial force is required and a high degree of damping is a desirable feature. A further advantageous feature of the described embodiments is the high mechanical work efficiency given by these transmissions compared with cylinder/piston hydraulic systems. As the size of the latter decreases the proportion of the stroke energy taken up by sliding friction of the seals increases. The transmissions described above, however, are estimated to have greater than 90% efficiency for bore sizes of less than 1 $mm^2$.

Modifications within the scope of the invention may be readily effected by those skilled in the art. For example, a flat coil spiral of unshrunken heat shrink will unwind when compressed fluid is fed into it. This may be employed as a device or actuator. The coil characteristics may be improved by heating it while constrained. Another actuator device can be formed by a section of the heat shrink material being formed into a concertina structure by enclosing a coil spring in the lumen of the tube before the heat shrink process is done. An internal folded metal strip can also be used. It is to be understood, therefore, that this invention is not limited to the particular embodiments described by way of example hereinabove.

In the preceding description of the invention, except where the context requires otherwise owing to express language or necessary implication, the word "comprise" or variations such as "comprises" or "comprising" is used in an inclusive sense, i.e. to specify the presence of the stated features but not to preclude the presence or addition of further features in various embodiments of the invention.

Further, any reference herein to prior art is not intended to imply that such prior art forms or formed a part of the common general knowledge.

The invention claimed is:

1. A method of manufacturing a fluid transmission, comprising:

forming a conduit for said fluid from heat shrink polymer tubing; and heat shrinking at least a portion of said heat shrink polymer tubing;

whereby a force can be transmitted by said fluid from a first or proximal end of said conduit to a second or distal end of said conduit.

2. A method as claimed in claim 1, further comprising forming at least one integral driver section comprising unshrunken or semishrunken heat shrink polymer tubing.

3. A method as claimed in claim 1, further comprising forming at least one integral driven section comprising unshrunken or semishrunken heat shrink polymer tubing.

4. A method for manufacturing a fluid transmission, comprising:

selectively masking a length of heat shrink polymer tubing; and heating said heat shrink polymer tubing to shrink a portion or portions of said heat shrink polymer tubing that is not masked;

whereby at least two unshrunken sections and at least one shrunken section are formed, to provide a driver bag and a driven bag with a fluid conduit therebetween.

5. An actuator, comprising:

four members, pivotably connected and forming a quadrilateral;

at least one expandable bag located between a pair of said members; and a fluid conduit in fluid communication with said expandable bag for expanding said bag by transmitting a fluid to said bag, said fluid conduit comprising heat shrink polymer tubing at least a portion of which is shrunken;

wherein expansion of said bag urges said pair of members apart.

6. An actuator as claimed in claim 5, wherein said quadrilateral is a parallelogram or a trapezium.

7. An actuator as claimed in claim 5, wherein said actuator is one of a plurality of like actuators coupled to form a complex or compound actuator.

8. An actuator as claimed in claim 5, further comprising a releasable magnetic latch for impeding said actuator until sufficient force is generated by said actuator to overcome said latch.

9. A device comprising an actuator as claimed in claim 5.

10. A device as claimed in claim 9, wherein said device is a toy or doll and said actuator is arranged to actuate movement of a portion of said toy or doll.

11. A device as claimed in claim 9, wherein said device is a camera, a robot, a microscope or a mobile telephone.

* * * * *